US009927450B2

United States Patent
Pollack et al.

(10) Patent No.: US 9,927,450 B2
(45) Date of Patent: Mar. 27, 2018

(54) TUBE CHARACTERIZATION STATION

(71) Applicant: Siemens Healthcare Diagnostics Inc., Tarrytown, NY (US)

(72) Inventors: Benjamin Pollack, Budd Lake, NJ (US); Ryan German, Riverdale, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 130 days.

(21) Appl. No.: 14/773,222

(22) PCT Filed: Mar. 7, 2014

(86) PCT No.: PCT/US2014/021572
§ 371 (c)(1),
(2) Date: Sep. 4, 2015

(87) PCT Pub. No.: WO2014/138533
PCT Pub. Date: Sep. 12, 2014

(65) Prior Publication Data
US 2016/0025756 A1    Jan. 28, 2016

Related U.S. Application Data

(60) Provisional application No. 61/775,106, filed on Mar. 8, 2013.

(51) Int. Cl.
*G01N 35/00* (2006.01)
*G01N 35/04* (2006.01)
*G01N 35/02* (2006.01)

(52) U.S. Cl.
CPC . *G01N 35/00732* (2013.01); *G01N 35/00603* (2013.01); *G01N 35/026* (2013.01);
(Continued)

(58) Field of Classification Search
CPC ...... G01N 35/026; G01N 35/02; G01N 35/04; G01N 35/00; G01N 35/00732
USPC .............................. 422/65, 63, 50
See application file for complete search history.

(56) References Cited

U.S. PATENT DOCUMENTS 3,706,305 A    12/1972  Berger et al.
3,807,955 A *  4/1974  Note, Jr. ............... B01L 3/5082
                                              206/519
(Continued)

FOREIGN PATENT DOCUMENTS

WO       2012/125291 A1    9/2012
WO       2012/158541 A1    11/2012
WO    WO 2013/070756   *   5/2013   ............. G01N 35/04

OTHER PUBLICATIONS

PCT International Search Report and Written Opinion dated May 28, 2014 (20 Pages).

*Primary Examiner* — Christine T Mui

(57) ABSTRACT

Systems and methods for use in an in vitro diagnostics setting may include an automation track, a plurality of carriers configured to carry a plurality of sample vessels along the automation track, and a characterization station including a plurality of optical devices. A processor, in communication with the characterization station, can be configured to analyze images to automatically characterize physical attributes related to each carrier and/or sample vessel. A method may include receiving a plurality of images from a plurality of optical devices of a characterization station, wherein the plurality of images comprise images from a plurality of perspectives of a sample vessel being transported by a carrier, automatically analyzing the plurality of images, using a processor, to determine certain characteristics of the sample vessel, and automatically associating the characteristics of the sample vessel with the carrier in a database.

29 Claims, 21 Drawing Sheets

(52) U.S. Cl.
CPC ... *G01N 35/04* (2013.01); *G01N 2035/00752* (2013.01); *G01N 2035/0406* (2013.01); *G01N 2035/0467* (2013.01); *G01N 2035/0491* (2013.01); *G01N 2035/0493* (2013.01); *G01N 2035/0494* (2013.01)

(56) References Cited

U.S. PATENT DOCUMENTS

| | | | |
|---|---|---|---|
| 4,828,716 A * | 5/1989 | McEwen | B01L 3/50215 210/104 |
| 5,138,868 A | 8/1992 | Long | |
| 6,329,139 B1 | 12/2001 | Nova et al. | |
| 6,599,476 B1 * | 7/2003 | Watson | B65G 47/1471 141/1 |
| 2001/0029030 A1 | 10/2001 | Alnemri | |
| 2002/0147515 A1 | 10/2002 | Fava et al. | |
| 2008/0156114 A1 | 7/2008 | Justin et al. | |
| 2010/0049358 A1 | 2/2010 | Koch et al. | |
| 2010/0129262 A1 | 5/2010 | Shanafelter | |
| 2010/0136632 A1 | 6/2010 | Lipscomb | |
| 2010/0184056 A1 | 7/2010 | Weinberger et al. | |
| 2010/0236445 A1 * | 9/2010 | King | B60L 13/003 104/130.03 |
| 2011/0245061 A1 * | 10/2011 | Haechler | B04B 13/00 494/8 |
| 2011/0268329 A1 | 11/2011 | Pronkine | |
| 2012/0067887 A1 | 3/2012 | Eikmanns et al. | |
| 2012/0190053 A1 | 7/2012 | Christ et al. | |
| 2012/0196320 A1 | 8/2012 | Seibel et al. | |
| 2013/0023060 A1 | 1/2013 | Klaunik et al. | |
| 2014/0305227 A1 * | 10/2014 | Johns | B01D 21/262 73/863.01 |

\* cited by examiner

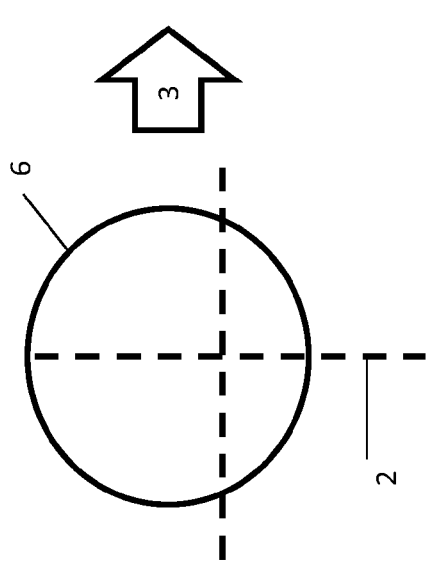
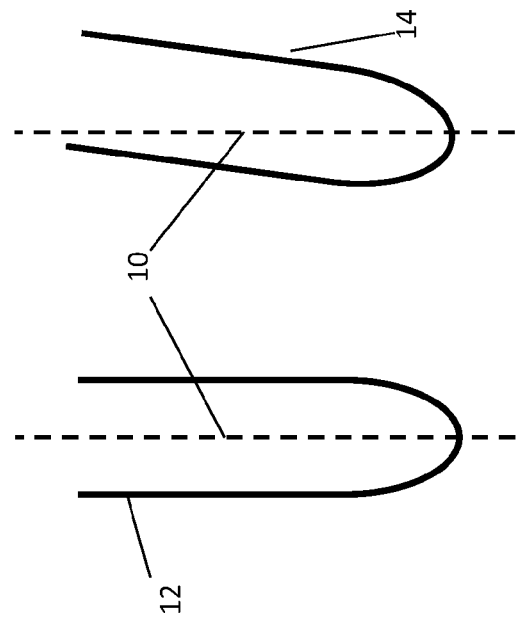
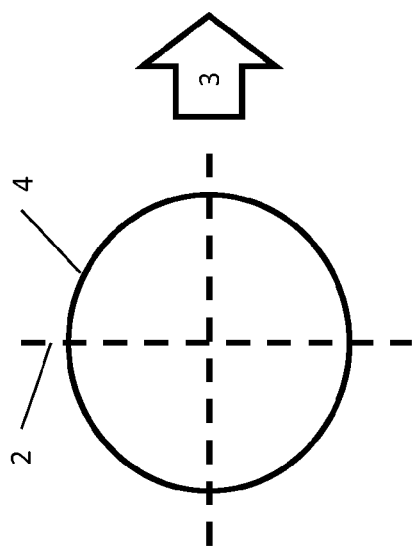
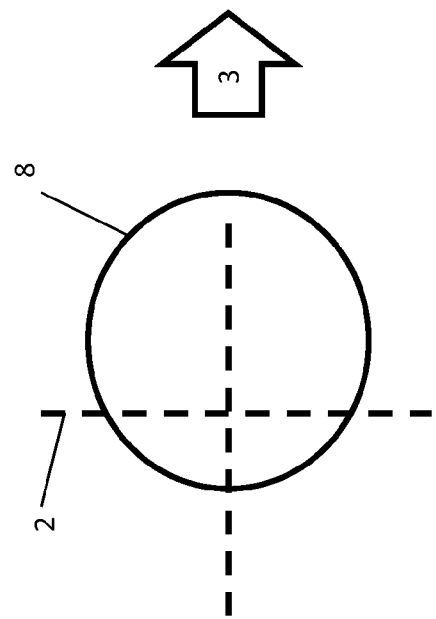
FIG. 1

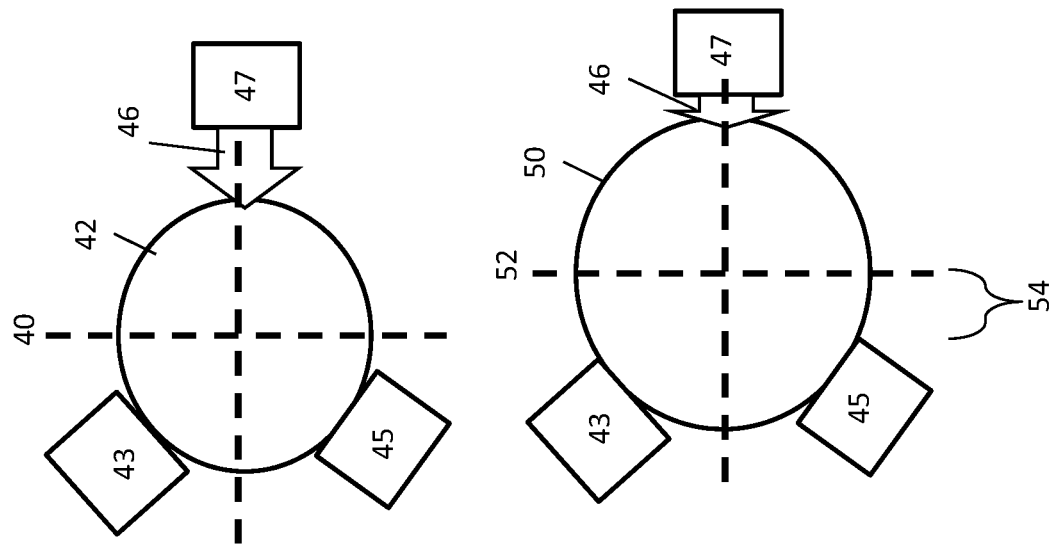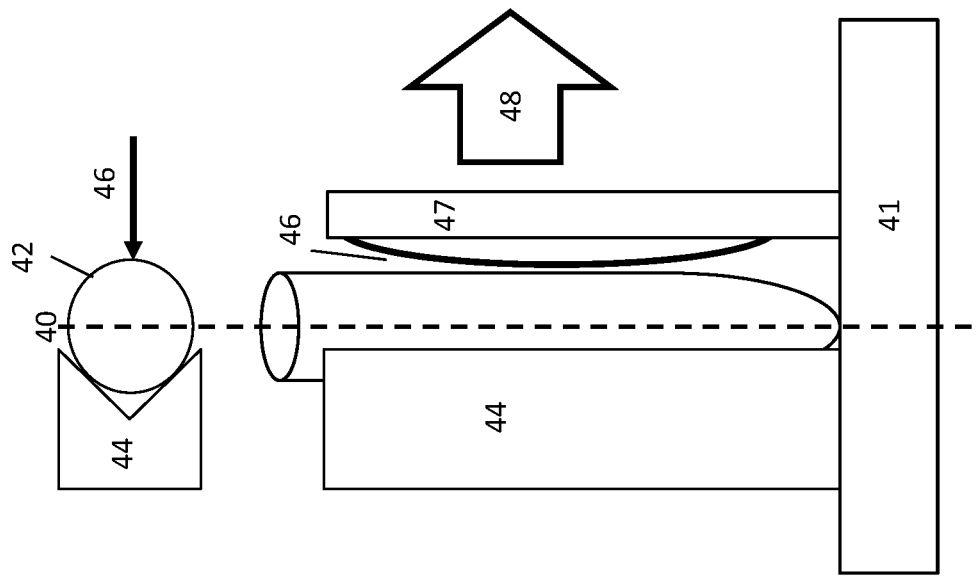
FIG. 3

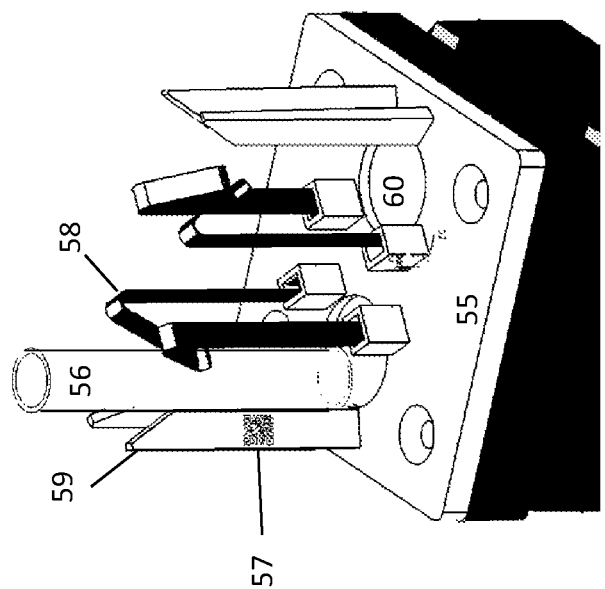
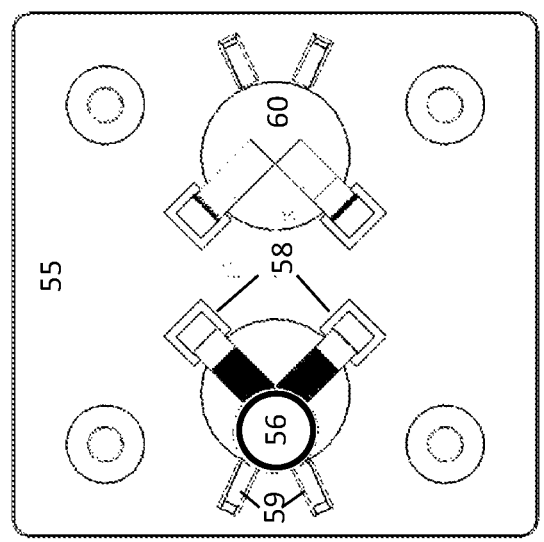
FIG. 4

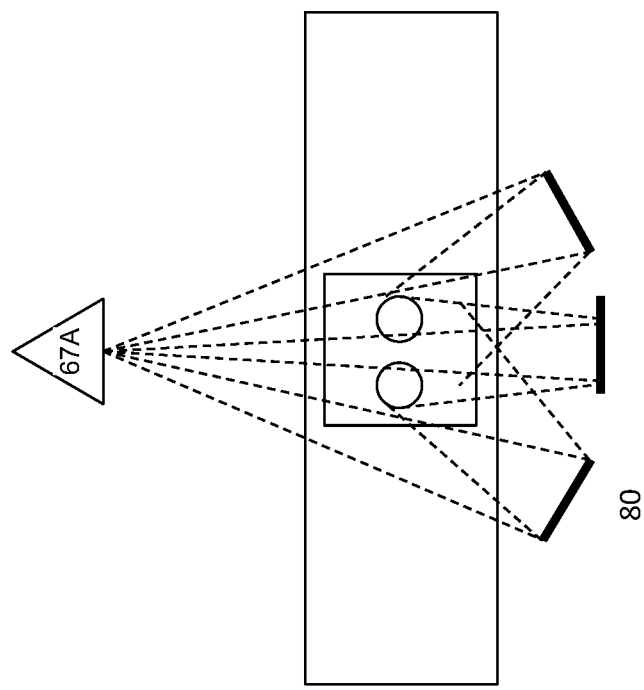
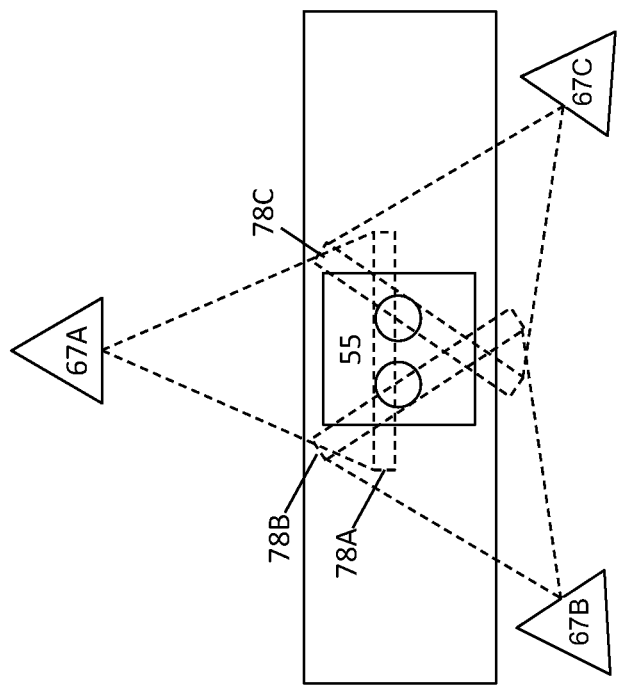
FIG. 9B
FIG. 9A

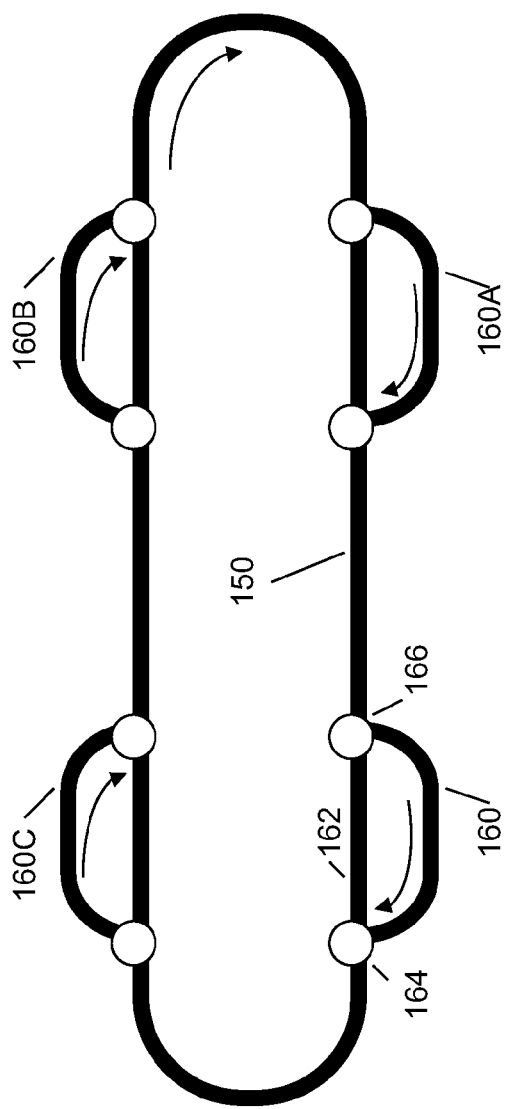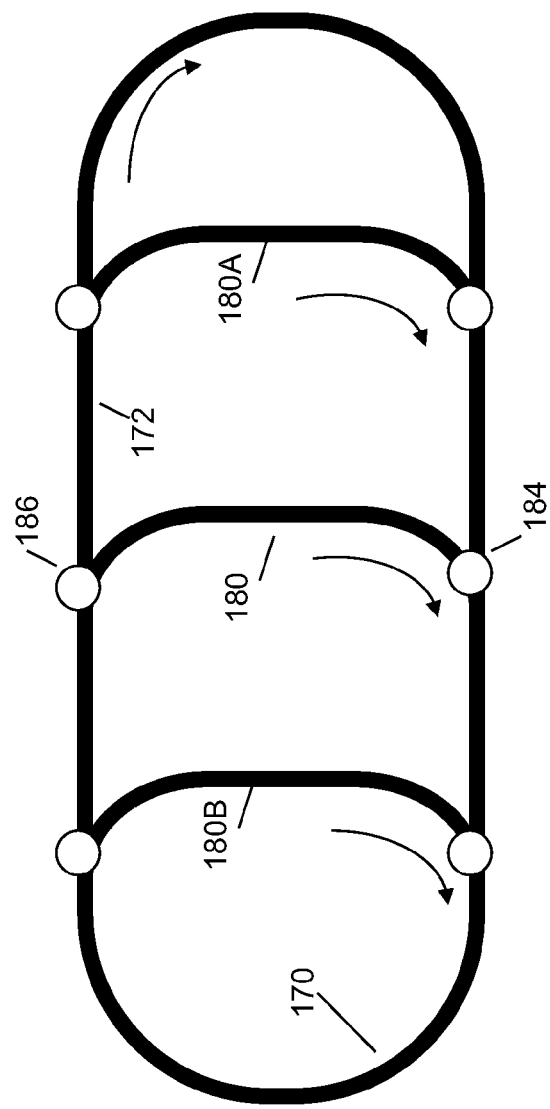

TUBE CHARACTERIZATION STATION

CROSS-REFERENCE TO RELATED APPLICATIONS

This application claims priority to U.S. provisional application Ser. No. 61/775,106 filed Mar. 8, 2013, which is incorporated herein by reference in its entirety.

TECHNOLOGY FIELD

The present invention relates in general to an automation system for use in a laboratory environment and, more particularly to systems and methods for assisting in the transport and interaction with patient samples for in vitro diagnostics in a clinical analyzer. Embodiments of the present invention are particularly well suited, but in no way limited to, systems and methods for optically characterizing carriers and patient samples or other objects being transported to determine how to further handle samples or objects.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from sample vessels and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations.

An automation system for use with analyzers in an IVD environment moves tubes containing sample specimens between different stations within an analyzer or between analyzers. One common way to move these samples is by using passive carriers, such as pucks, along a friction track. Commonly, these automation tracks do not provide a large degree of precision when positioning samples. For example, passive pucks may be singulated and positioned mechanically using hard stops within the track. Singulation prongs may hold a puck in place once the puck has traversed the automation track to approximately the needed location. However, these prongs may not be adjustable for each puck and positioning a puck at a hard stop may not necessarily cause samples carried by the pucks to be repeatedly positioned relative to instruments, such as pipettes, along the automation track.

While hard stops may be used to position a puck with relative repeatability, devices that interact with the sample, such as pipettes, may require precise orientation and positioning of the sample at a given location on the track. The position and orientation of each sample may vary relative to the hard stops from puck to puck. For example, the manufacturing tolerances between two pucks may prevent a repeatable location of the bottom of the tube relative to a given singulation point. In addition, tubes may shift within the grasp of a puck, such as by tilting, or moving off center from a holding location within the puck as the puck traverses the automation or at the time an operator places the tube into the puck.

One common way to provide somewhat repeatable positioning of a sample tube employs a holder on a puck with self-centering springs. A self-centering spring mechanism can include three or more springs that provide horizontal forces relative to one another to engage the walls of a sample tube to hold the tube approximately in the center of the mechanism. Self-centering springs may be expensive to manufacture with the tolerances necessary to provide self-centering action. For example, in designs where self-centering springs include multiple springs that push relative to one another, the self-centering action requires the relative forces of the springs to be approximately equal. Furthermore, self-centering springs may only be designed to allow tubes with a relative range of sizes that may be narrower than desired. Self-centering springs may also be poorly suited for maintaining the position of a tube while undergoing large forces as the puck travels around an automation track.

Different hospitals or laboratories may also use different size sample tubes. Within the IVD industry, there may be several standard sizes of available sample tubes. Different laboratories may use a variety of sample tubes or a subset of those available, according to their needs and available inventory. Conventional automation systems have a difficult time using a wide range of available sample tubes. While self-centering springs may allow a range of sample tubes to be used, the effective range of self-centering springs may be limited. In addition, when a range of tubes is used, a typical automation system does not know which size tube is used for each sample. This information can be manually associated with each sample, but requires additional operator steps which may be undesirable.

To determine various properties of samples in sample tubes, various sensors may be used throughout the IVD environment to allow assessment of characteristics important to each instrument. This information is typically sensed in an on-demand basis. For example, a pipette may utilize a liquid level sensor that measures the capacitance or other electrical properties of a pipette tip as it is inserted into a liquid sample during aspiration. A robot arm used in a sample handling unit may include tips that are designed to accept a range of tube diameters. These tips may include sensors or feelers to assist the robot arm in capturing a tube without breaking it. A barcode scanner can be placed at different decision points throughout the IVD environment, allowing a laser-based barcode reader to read information about the identity of each tube once the tube is stopped and rotated to bring a barcode into view of the reader. While the stop-and-check approach to barcode scanning can ensure that each sample is appropriately handled at each decision point, this process may be slow and result in long queues at each decision point.

Accordingly, current methods for handling ranges of sample tube types and for sensing the properties of samples in tubes may be slow or cumbersome, creating a potential bottleneck for increasing throughput or decreasing turn-around-times of samples that are processed by an automation system and related instruments.

SUMMARY

Embodiments of the present invention may address and overcome one or more of the above shortcomings and drawbacks by providing devices and systems for characterizing physical attributes of carriers and/or the sample vessels being transported by the carriers in an automation system. This technology is particularly well-suited for, but by no means limited to, transport mechanisms in an automation system for use in an in vitro diagnostics (IVD) environment.

According to one embodiment of the invention, an automation system for use in an in vitro diagnostics setting includes an automation track, a plurality of carriers configured to carry a plurality of sample vessels along the automation track, and a characterization station including a plurality of optical devices. A processor, in communication with the characterization station, is configured to analyze images to automatically characterize at least one physical attribute related to each carrier.

According to another embodiment of the invention, a characterization station is configured for use with an automation system and includes a plurality of optical devices configured to capture one or more images of a carrier on an automation track a processor configured to analyze the one or more images to determine at least one physical attribute of the carrier or an object being transported by the carrier. According to one aspect of some embodiments, the processor can be configured to determine which, if any, of a plurality of slots in each carrier is occupied.

According to one aspect of some embodiments, the physical attributes that can be characterized can include: an orientation of at least one sample vessel relative to each carrier, where the orientation can further include at least one of a linear offset or rotational offset relative to a nominal position; physical dimensions of at least one sample vessel carried by each carrier; an identification of a type of sample vessel carried by each carrier; an identification of a type of each carrier; an identification of the shape of the bottom of a sample vessel carried by each carrier; a determination of whether a sample vessel carried by each carrier is properly seated; a temperature of a sample vessel carried by each carrier; a fluid level or fluid volume of a fluid contained in a sample vessel carried by each carrier; a determination of the presence of at least one of the following within a blood sample carried by at least one carrier, a gel barrier, clotting, hemolysis, icterus, and lipemia; an identification whether a cap is placed on a sample vessel carried by each carrier; an identification of at least one of a color and a type of the cap; an identification whether a tube-top cup is placed on a sample vessel carried by each carrier; an identification of a type of the tube-top cup.

According to another aspect of some embodiments, the processor can be configured to analyze images to read barcode information encoded on at least one of a sample vessel, carried by each carrier, and each carrier.

According to yet another aspect of some embodiments, the plurality of optical devices of the characterization station can include a plurality of cameras placed at different positions relative to an imaging location of each carrier. The plurality of optical devices of the characterization station can include at least one camera and one or more mirrors placed in an image plane of the at least one camera to provide different perspectives of each carrier. The plurality of optical devices of the characterization station can also include optics with depths of field substantially concurrent with an expected position of features of each carrier. The plurality of optical devices of the characterization station include at least one camera configured to view each carrier horizontally and at least one camera configured to view each carrier from above.

According to yet another aspect of some embodiments, the automation track can include a linear synchronous motor and the processor is further configured to calibrate a position of each carrier within the automation track.

According to another aspect of some embodiments, each of the carriers can include a plurality of slots, each configured to receive one of the plurality of sample vessels. The characterization can be configured to move each carrier so that an occupied slot of the plurality of slots is located in an image field of the plurality of optical devices prior to characterization of the at least one attribute.

According to another embodiment of the invention, a method of characterizing sample carriers in an automation system includes steps of receiving a plurality of images from a plurality of optical devices of a characterization station, wherein the plurality of images comprise images from a plurality of perspectives of a sample vessel being transported by a carrier, and automatically analyzing the plurality of images, using a processor, to determine certain characteristics of the sample vessel. The method further includes automatically associating the characteristics of the sample vessel with the carrier in a database.

According to one aspect of some embodiments, the method includes utilizing the orientation of the sample vessel to adjust the placement of the carrier at subsequent stations within the automation system. According to another aspect of some embodiments, the method includes determining whether the sample vessel occupies a first slot in the carrier that is located in intersecting image planes of the plurality of images and moving the carrier if not. The method may further include determining if certain features of the sample vessel are obscured in the plurality of images and repositioning the carrier in response to the determination. The method may further include determining if certain features of the sample vessel are obscured in the plurality of images and repositioning the sample vessel within the carrier in response to the determination. According to another aspect of some embodiments, the method may also include adjusting one of the positions of the carrier relative to an automation track and the position of the sample vessel if the processor determines that the plurality of images contain insufficient information to determine the certain characteristics.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1 is a diagrammatical view of various types of positioning attributes that may be characterized in some embodiments;

FIG. 3 is a top and side view of an exemplary carrier for use with some embodiments;

FIG. 4 is a top view and perspective view of an exemplary carrier for use with some embodiments;

FIG. 9A is a diagrammatic top view of an exemplary characterization station for use with some embodiments;

FIG. 9B is a diagrammatic top view of an exemplary characterization station for use with some embodiments;

FIGS. 13A and 13B are diagrammatic views of track geometries that can be used with the automation system embodiments disclosed herein;

DETAILED DESCRIPTION

Figure 2:
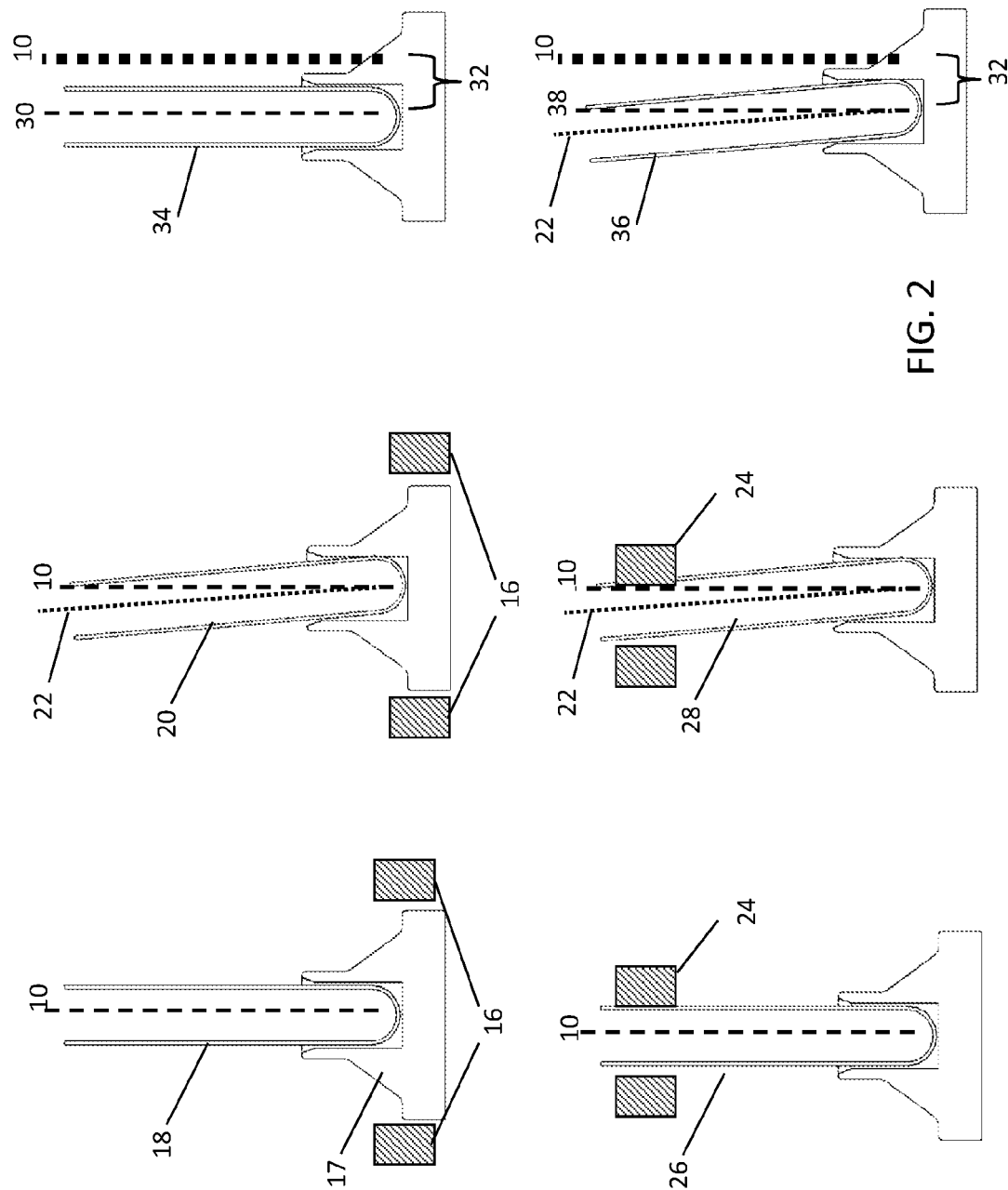
FIG. 2 is a diagrammatical view of various types of positioning attributes or errors that may be characterized and corrected with some embodiments.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refer to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention may overcome some of the shortcomings of the prior art by providing a common optical instrument suitable for characterizing the physical attributes of each carrier and sample tube being carried by that carrier. A characterization station may be placed in a suitable location in an automation system, allowing a single characterization of a sample vessel and its carrier. The identity and attributes of the sample vessel or combination of sample vessel and carrier can be associated with the patient sample in a local database. This information about the physical attributes of the sample vessel can be used in each processing station throughout the automation system to quickly determine how the processing station should interact with the patient sample, without requiring accurate sensors to be used at each processing station.

A characterization station can include a plurality of optical devices, such as cameras or mirrors. Cameras can include visible light, IR, or UV light cameras, and can be used in conjunction with appropriate lighting sources. In some embodiments, mirrors are also used to allow additional information to be captured in a single image, allowing fewer cameras to be used. Optical devices can be placed in different locations within the characterization station to allow different perspectives to be captured in different images. This may allow a substantially 360° view to be compiled for each sample vessel or carrier. In some embodiments, a camera can also be placed facing downward to provide an overhead view of each sample vessel. The images captured can then be analyzed using an image processor, which may include a CPU or DSP. The image processor can identify salient features within the images to evaluate the identity of each sample vessel or carrier, as well as characterize certain physical attributes of each sample vessel. These attributes may include, for example, the height and diameter of the tube, whether the tube currently has a cap, the color or other identifying characteristics of the cap, which may convey the type of sample, whether a tube-top cup is placed in the sample vessel and the type of tube-top cup used, the orientation of the sample vessel relative to the carrier (which may include the tilt, height, and/or X-Y translation of the vessel relative to the carrier, or any combination thereof), and the height of any liquid in the sample vessel. Other attributes of sample vessels or carriers that can be determined from optical sensors and images processed are discussed throughout. The image processor may also look for identifying marks in the images, including barcode information. The image processor may analyze barcode information to identify the sample and associate the physical attributes determined during image analysis with that sample.

By associating the physical attributes of each sample vessel with the identity of the sample, when subsequent stations process that sample, the stations may have access to the recorded physical attributes of the sample vessel and utilize this information during sample processing, without requiring additional sensors at each processing station. For example, the orientation of each sample relative to each carrier can be used by subsequent processing stations to identify an exact location of the center of each sample vessel before a carrier arrives at that processing station. This may allow a processing station to make a slight adjustment to the position of the carrier relative to the position of instruments, such as pipettes, that interact with the sample to allow successful interaction with non-centered samples. In some embodiments, this may eliminate the need for self-centering springs, allowing cheaper or more robust sample holders to be used with each carrier.

In some embodiments, carriers may be provided that do not rely on hard singulation stops to come to rest at a desired stopping location. Carriers may further include the ability to precisely stop at a desired offset from an absolute stopping location, allowing a sample tube to be positioned independently of a hard stop. By characterizing the location of the sample relative to a carrier and positioning a carrier relative to an offset calculated from this characterization, a sample tube may be precisely and reliably positioned relative to instruments, such as pipettes, that may require reliable positioning of samples prior to operation. Furthermore, in some embodiments, a wide range of tube sizes may be used, and an offset may be used to reliably position the center of each sample tube relative to an instrument.

In the prior art, hard stops were used to determine the stopping location of a carrier, such as a puck. However, the position and orientation of sample tubes may vary between carriers relative to the position of the hard stop. As a result, the resting position orientation of a sample tube may vary from a nominal position. There are three primary ways in which the position and orientation of a sample tube may vary from a nominal position as shown in FIG. 1. FIG. 1 shows the relative position of a line of action to the walls of the sample tube. A line of action can be considered the path that a probe tip will take when interacting with a tube. A line of action may be represented by crosshairs (such as line of action 2) when viewing the horizontal plane in a top-down fashion or as a vertical line (such as line of action 10) when viewing of the line of action from the side. Positioning errors can be considered a deviation of the center of a tube relative to the line of action of an instrument in the horizontal plane, while tilt errors can be considered deviations of the center of a tube relative to the line of action from the side.

Tube 4 shows an ideal position (i.e. nominal) where the center of tube 4 coincides with the line of action 2. Tube 4 travels in a direction 3, along an automation track. In this example, tube 4 has come to rest at a nominal position. Tube 6, however, is positioned with an error in the lateral direction from the nominal position of the line of action 2. Tube 8 is positioned with an error in the longitudinal direction (i.e., along the direction of travel 3) relative to the nominal position where the center of tube 8 would be coincident with line of action 2. Tubes 6 and 8 illustrate X and Y positional errors. Tubes may also be described as sample vessels, as some embodiments can work with various shaped sample vessels that may be used to transport samples in an IVD environment.

Tube 12 shows the ideal, nominal tilt of a tube relative to the line of action 10. Here, tube 12 is positioned in the nominal vertical direction. Tube 14 has a tilt error relative to the line of action 10, illustrating an extreme angle of tilt that may be experienced by a tube that is positioned at an instrument in an automation system. The positional errors of tubes 6 and 8 and the tilt error of tube 14 are not ideal and may make it difficult to operate an instrument. For example, a pipette may clip the wall of the sample tube interfering with its operation. Furthermore, if smaller tubes are used, it may be difficult or impossible for that tube to interact with an instrument due to the position or tilt errors illustrated in FIG. 1.

FIG. 2 illustrates the effect of using hard stops to position centers of tubes relative to lines of action. Hard stops 16 stop carrier 17 along an automation track at a predetermined location. Carrier 17 carries a tube, such as tube 18. Tube 18 illustrates a nominal position for the center of the tube relative to line of action 10, which may be the line of action of a pipette at a testing station. Tube 20, however, reveals a potential issue using hard stops 16 to stop a carrier at the base of the carrier 17. Center line 22 at the center of tube 20 is tilted relative to line of action 10. Therefore, tube 20 has a tilt error relative to nominal.

Hard stops 24 illustrate another potential issue using hard stops to position the stopping point of a tube. Engaging a tube using hard stops may also damage or jar a tube and may be problematic for any number of reasons other than introducing positional errors, such as risking tipping a carrier over, which may cause the contents of a sample tube to spill. Tube 26 engages hard stops 24 at a nominal position and orientation. The center of tube 26 is coincident with line of action 10. However, tube 28 comes to rest at a tilt relative to line of action 10. In some instances, tube 28 may be knocked into a tilted orientation due to the force used to stop the tube by hard stops 24. Center line 22 has a tilt error relative to the nominal position.

Tubes 34 and 36 illustrate how tubes may come to rest with a positional error relative to nominal that may be introduced by any number of causes. For example, the best line of action available for tube 34, which may be centerline 30, may deviate from the line of action 10 of an instrument by an offset 32. This offset 32 is a positional error. In this instance, a pipette operating along the line of action 10 will completely miss the contents of sample tube 34. Offset 32 may be introduced because carrier 17 stopped too soon, or because tube 34 is off center from the center of carrier 17. For example, carrier 17 may include a holding mechanism that is designed to operate with a plurality of different sizes of tubes. Larger tubes may result in a different location of the center of the tube compared to the center of a smaller tube. It should be appreciated that for smaller diameter tubes the likelihood that an offset 32 will be outside the diameter of the tube is increased. Accordingly, if smaller tubes or tube-top cups are used, the margin of error for offset 32 may be reduced proportionally.

Tube 36 has a positional error as indicated by offset 32 between the nominal line of action 10 (e.g., the nominal resting position of tube 36) of an instrument and the nominal line of action 38 for tube 36. It should be noted that tube 36 also has a tilt error as indicated between the center line 22 and the nominal line of action for the tube, line 38. Line 38 indicates that a pipette could still be inserted into tube 36 to reach fluids contained in the tube, even though a tilt has been introduced. While this tilt may not be ideal because the range positions that can be used for a line of action into the tube is limited, in some embodiments, the offset 32 can still be used to position the line of action of a pipette at a viable line of action within the tube by removing the offset.

FIG. 3 shows an exemplary embodiment of the tube carrier portion of a carrier that may be suitable for reducing tilt errors in the positioning of a tube. Tube 42 includes a centerline 40. Tube 42 is carried by carrier 41, which includes a V-shaped block 44 that allows tube 42 to be self-centered in the lateral direction when held in place by a force in the longitudinal direction, which may be provided by a spring, such as leaf spring 46. Tine 47 may support leaf spring 46. Because of the V-shaped block 44, regardless of the diameter of tube 42, a force in the longitudinal direction can force the tube into the recess of the V-shaped block and orient the tube vertically at the lateral center point of the recess. Such a design can utilize a single spring 46 which may be a single strong spring which may hold tube 42 into block 44 with sufficient force that carrier 41 may undergo any reasonably desired range of acceleration while traversing the automation track without movement of tube 42. Furthermore, because only a single spring need provide a force, the tolerance needed in producing and selecting the spring may be very low. In contrast, many self-centering spring designs require various springs to provide competing forces, such that the springs must be tightly toleranced to provide balanced spring forces to ensure that the tubes are held in the center. In a carrier 41, spring 46 works with block 44 to reliably center tube 42 in the lateral direction, but not necessarily in the longitudinal direction. Larger or smaller tubes may sit in block 44 with a center that moves fore or aft relative to carrier 41 when carrier 41 is oriented in a direction of travel 48.

Block 44 includes a V-shaped channel that is oriented in a vertical direction, forming a vertical spine. Because tubes generally have substantially parallel walls, a force pushing the tube into this V-shaped spine will generally orient the centerline of the two parallel walls to the orientation of the spine, as this is the lowest energy state and resting place of the tube within the V-shape. In this manner, block 44 may provide advantages over traditional self-centering spring designs. First, a sufficiently large force will keep tube 44 oriented in a substantially vertical direction, therefore minimizing or eliminating tilt errors in the orientation of the tube. Furthermore, even with a poorly toleranced spring 46, tube 44 will be substantially oriented at the center of block 44 in the lateral direction. Accordingly, carrier 41 need only be moved to a proper location in direction 48 to position tube 42 in substantially the nominal location for a line of action of a given instrument within an automation system.

Block 44 may be replaced with two tines 43 and 45 that provide a V-shaped recess into which a tube may be placed, while allowing the backside of the tube to be viewed. For example, the gap between tines 43 and 45 may allow viewing of any barcode information on tube 42. The gap between tines 43 and 47 and between tines 45 and 47 may also allow reading of any barcode information viewable on the sides of tube 42.

A larger tube 50 may also be placed between lines 43, 45, and 47. As can be seen in FIG. 3, the centerline 52 is moved in a fore direction relative to centerline 40 of tube 42. This is because the larger diameter of tube 50 causes tube 50 to sit further forward in the V-shape of tines 43 and 45 and because the larger diameter causes the centerline to sit further from the points of contact with tines 43 and 45. Spring 46 is more compressed when holding larger tube 50. While centerline 52 is moved forward from centerline 40 by a distance 54 due to the difference in sizes of the tubes, it should be appreciated that both tube 42 and tube 50 are both oriented substantially parallel to tines 43 and 45 and centered in the lateral direction between tines 43 and 45. Accordingly, the distance 54 between the centerlines can be corrected by using a different offset when positioning carrier 41 at an instrument along the automation system to align the centerline of each instrument with the centerline of each tube.

FIG. 4 shows a top view and a perspective view of an exemplary carrier for use with some embodiments of the present invention. Carrier 55 is a dual slot carrier, allowing single samples to be carried in either of two slots. In some embodiments, multiple samples may be simultaneously carried. Multiple slot carriers are described in further detail in U.S. provisional patent application Ser. No. 13/64,620, filed Oct. 11, 2013, which is incorporated herein in its entirety. A sample vessel 56 may include a sample tube that carries a patient sample or other fluid. Sample vessel 56 may be held in place by springs 58, which provide a common spring force to press sample tube 56 into vertical tines 59. Tines 59 act as a V-block, allowing tube 56 to be oriented securely in a vertical direction. Meanwhile, slot 60 may remain unoccupied.

Carrier 55 may assist the automation system by providing a secure, repeatable orientation and position of tube 56 relative to the structures of carrier 55. By detecting the orientation of tube 56 with respect to carrier 55, subsequent processing stations can utilize an offset to position carrier 55 and a location that allows instruments to interact with sample vessel 56. This orientation may be detected by image analysis performed by a processor coupled to the characterization station.

A characterization station may analyze images of tubes in carriers, such as carrier 55, to determine various physical properties of the carrier and sample vessels being carried. For example, the orientation of a sample vessel within the carrier, including the relative position of the sample vessel to the carrier can be characterized through optical analysis. Similarly, physical dimensions of the sample vessels being carried can also be characterized. Whether these sample vessels include caps or tube-top cups may also be determined using the characterization station. The height of fluid contained in the vessels may also be optically characterized. In addition, barcodes on the sides of sample vessels can be read by providing various perspectives to allow the barcode information to be optically read without requiring that the tube be rotated or otherwise carefully placed in a given orientation by an operator.

Figure 5:
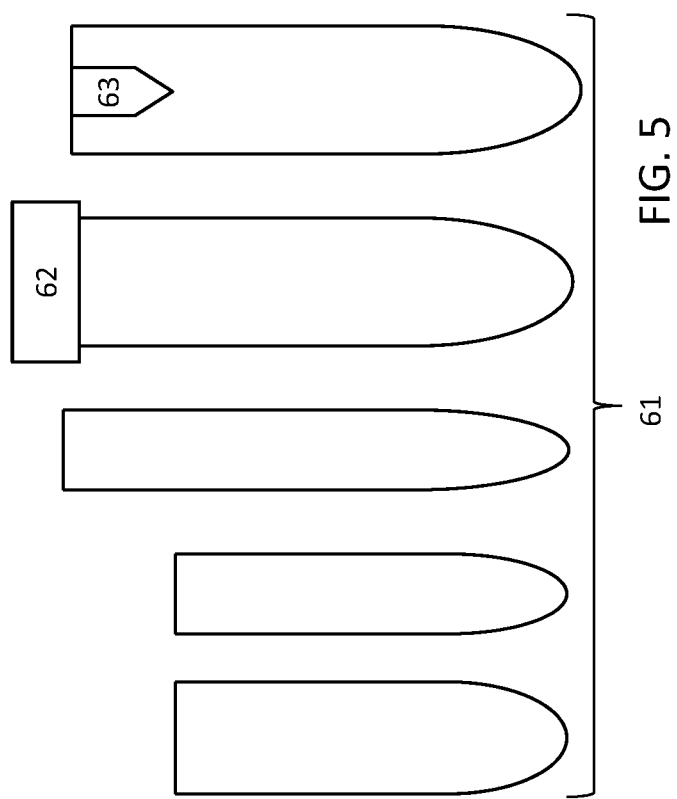
FIG. 5 is a side view of a group of exemplary sample vessel types for use with some embodiments.

Sample vessels used with carrier 55 may include a range of different sizes of sample tubes. FIG. 5 illustrates some exemplary tube configurations that may be used with the sample carrier. A range of sample tubes 61 may be inserted into slots of carrier 55. Some tubes may be short, while others may be tall. Some tubes may be narrow, while some tubes may be wide. Furthermore, some tubes may include a cap 62, which requires removal prior to subsequent processing. When a characterization station detects the presence of a cap 62, the characterization station may inform the automation system that the sample carrier must be routed to a de-capping station prior to subsequent processing. The color or pattern of the cap may also be identified optically. In some embodiments, the cap color or pattern may indicate the type of sample being transported (e.g., whole blood, urine, possibly infected, etc.) In some embodiments, the characterization station can identify the pattern, color, and/or type of cap on a sample vessel to identify the type of sample being carried.

Some tubes may also include a tube-top cup 63. By performing image analysis at the characterization station, the presence of a tube-top cup may be noted in the image, allowing that tube to be identified as having a tube-top cup. In some embodiments, the characterization station can identify the size/type or position of the tube-top cup to further identify the center and positional tolerances needed when a pipette interacts with the tube-top cup. Subsequent processing stations may utilize this information to change how they interact with the sample stored in tube-top cup 63. A tube-top cup can be a narrow, substantially shallower vessel that fits into the top of a larger sample tube, allowing smaller amounts of sample liquid to be stored in a vessel with a suitable aspect ratio for interacting with a pipette. When a characterization station notes the presence of tube-top cup 63, its location within the sample vessel can be noted and used to accurately position the tube-top cup at subsequent processing stations. A tube-top cup may be substantially less than 1 cm in diameter, and may require additional precision in locating the center of the tube-top cup when interacting with subsequent processing stations. The presence of a tube-top cup may also necessitate special handling of a carrier as it traverses the automation track, such as requiring lower cornering speeds of a carrier transporting a sample in a tube-top cup.

In some embodiments, a processor that analyzes images associated with sample vessels at the characterization station may compare the detected physical dimensions to a known set of available sample vessels, allowing the processor to select the type of sample vessel in the image. By limiting the available dimensions to a smaller set of discrete available dimensions, image analysis at characterization station may be improved. This may allow the characterization station to accurately identify which type of tube in set 61 to which the tube currently being characterized belongs.

Figure 6:
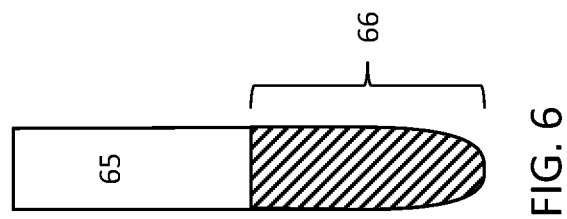
FIG. 6 is a side view of an exemplary sample vessel for use with some embodiments.

FIG. 6 shows an exemplary sample tube 65 with a sample fluid having a height 66. Optical devices in the characterization station can identify different coloration between the material of the sample tube 65 and the sample fluid or a meniscus line to identify the sample fluid height 66 during image analysis.

Figure 7:
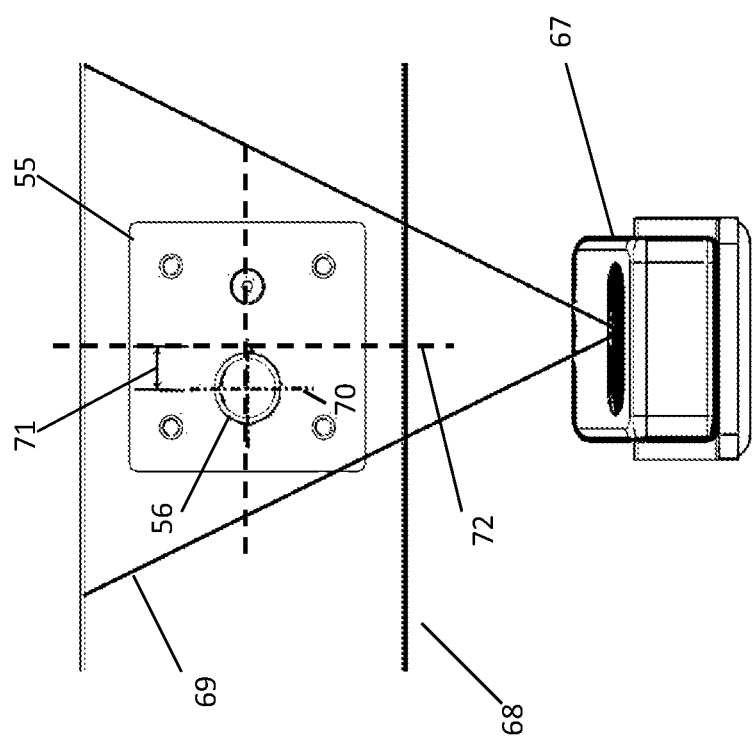
FIG. 7 is a top view of an exemplary characterization station for use with some embodiments.

FIG. 7 shows an exemplary characterization station that may be used to characterize offsets needed to position a tube at an optimal position on an automation track. The characterization station can include a plurality of optical devices 67 (only one shown for illustrative purposes) that capture images that may be analyzed by a processor to measure the distances between tubes and carriers relative to some known or expected position on the carrier. The optical measuring devices 67 can include any suitable optical devices, such as a camera with sufficient resolution and accuracy to characterize distances in an image (such as by mapping pixel distances relative to known distances in the real world). Other optical devices can include mirrors to allow a camera to view the tube from different perspectives (as explained below). Optical devices 67 generally include a plurality of imaging devices suitable for providing a plurality of perspective images of the carrier and sample vessels being carried thereon.

Optical device 67 can characterize carrier 55 and a tube 56 being carried by carrier 55. Carrier 55 travels along automation track 68, which may be any suitable automation track known in the art or disclosed herein. An individual optical device 67 can provide an image sufficient for measuring distances or reading barcodes within field of view 69.

In some embodiments, in addition to optical devices 67, additional sensors can be used in the characterization station. For example, a measuring device may project an infrared beam onto an object, allowing accurate measurements of the relative distances within the field of view. In some embodiments, a measuring device may include IR rangefinders or projection devices along with mono or stereoscopic cameras. This may allow the characterization station to measure distances in one dimension, two dimensions, or three dimensions. In some embodiments, a raster scan or a single slice of a scan can be used to measure a single distance of a tube surface relative to a nominal position along the direction of travel. In some embodiments, one or more LEDs on one side of automation track 68 and an electro-optical device, such as a camera or one or more photo detectors on the other side of the track can provide precise timing-based measurement of shapes and distances between portions of objects passing along the track. For example, precise timing when the fore and aft portions of a carrier pass a characterization station, and when the fore and aft portions of a tube pass the characterization station, can provide precise information about the relative location of the tube within the carrier. In some embodiments, an overhead camera may be used, which may provide a two-dimensional image and allow for a two-dimensional, X-Y measurement of the position and orientation of a tube relative to a carrier.

In some embodiments, a light source may be used in conjunction with one or more cameras to allow illumination of tubes and carriers or to provide distinguishable colors or patterns that may be used to provide additional detail to an image. For example, an IR light source can be used with an IR camera to provide detail in an image that may not be otherwise available from ambient light. In some embodiments, a monochrome grid may be projected to assist in viewing depth in an image. Furthermore, in some embodiments, the IR beam and an IR camera can be used in conjunction with another visible-light camera (that may be offset from the IR camera) to provide color and range information.

In addition, the light source may be offset from the viewing camera, which may allow distance information to also be gathered from the image in some embodiments, the optical system used may be similar to the system used by the Xbox Kinect vision system available from Microsoft Corporation. In some embodiments, three-dimensional information is gathered by the use of a plurality of cameras and/or a plurality of light sources.

In some embodiments, multiple cameras may be used to provide two or three dimensional information of the position orientation of the tube within a carrier, as well as providing more image details for a more robust measurement of offsets of the tube from a nominal position.

By analyzing, via a processor, images from optical device 67, the characterization station can measure a distance 71 between the observed centerline 70 of tube 56 and the expected centerline 72, which may coincide with the centerline or a known position relative to carrier 55. In some embodiments, a single carrier carries a single tube at the geometric center of the carrier in the longitudinal direction under nominal conditions. Observing a distance 71 between the actual centerline of a tube and the expected centerline of the tube may identify an offset that should be applied to carrier 55 when carrying tube 56 for each station the carrier visits. The next time a tube is inserted into carrier 55, a new offset 71 can be determined during another characterization. In some embodiments, a carrier/tube combination is characterized at least once for each tube that is inserted into a carrier. In some embodiments, a tube and carrier combination may be characterized multiple times as it traverses an automation system.

The term characterization station, as used herein, is any combination of components in the automation system that optically characterizes a carrier and/or a sample vessel being characterized. The optical characterization can include characterization of physical attributes, such as the dimensions of a carrier or sample tube, an identification of the type and status of a sample tube (e.g., capped, uncapped, having a tube-top cup, etc.), a characterization of the orientation of the sample vessel (which may include x-y-z location, tilt, etc.), a calibration of the orientation of the distances between a position of a tube, such as the tube's centerline, relative to other positions within the automation system, such as the leading edge of a carrier or a part of the carrier that is used to provide a reference position. In some embodiments, the characterization station can observe an orientation of a carrier or sample vessel/payload within a carrier where the orientation information includes at least one of a linear offset (e.g., X, Y, and/or Z translation offset) and a rotational (e.g., tilt, yaw, and/or roll) relative to a nominal position. The optical characterization can include optical identification of a sample tube or carrier by reading optical marks in images of the carrier or sample vessel.

In some embodiments, carriers can include optical marks, such as opaque or reflective marks or patterns, physical surfaces, such as leading edges or indentations, magnetic devices, or any other identifiable points on a carrier that may be used for reference points in a distance measurement. In some embodiments these include barcodes or 2-D digital marks, such as QR codes (such as QR code 57 shown in FIG. 4). In some embodiments, characterization stations perform measurements of tubes relative to reference points on a carrier using optical means, such as cameras or other optical devices disclosed herein. In some embodiments, optical devices can include a plurality of cameras or a camera with a plurality of mirrors that allow the camera to view a vessel from a plurality of perspectives to provide multiple images in a single image. In some embodiments, characterization stations may observe and characterize carriers and tubes using other means, such as magnetic measurement or physical measurement, such as providing feelers to note the distances between surfaces of a tube and a carrier. In some embodiments, radiation devices, such as x-ray or tomography devices, may be used to measure positions of tubes and surfaces of carriers to characterize carriers and/or combinations of carriers and tubes.

In some embodiments, imaging devices can be used in a characterization station to determine certain extrinsic or intrinsic properties of fluid samples contained in sample vessels. For example, an imaging device can capture an image that, when processed, reveals a level of the fluid sample. This may be useful for determining when a fluid level is getting low. Analyzer stations typically have subsystems to detect the fluid level in a tube. By bringing this capability to a central sensing device, the cost can be reduced and reliability increased (e.g., by using one high quality sensor instead of many—one per analyzer station—low quality sensors). In some embodiments, the characterization station can utilize the fluid level determined from an image, along with information about the type of sample to being observed (which may be determined optically or from the database based on a sample or carrier identification) to determine a sample volume. Using a combination of fluid level and the size and type of the sample vessel, a sample volume if can be readily calculated. In the prior art, analyzers generally do not detect insufficient sample volume until they attempt to aspirate fluid for a test and discover that there is not enough (usually by detecting that they have aspirated air). By detecting insufficient sample volume as soon as the sample is imaged at the characterization station, it is possible to notify the lab that another vessel of a patient's bodily fluid will be needed much earlier. This early notification can make a critical difference in patient care and may make it easier for the lab or hospital to manage errors.

In some embodiments, imaging devices in a characterization station can determine the shape of the bottom of a tube. This information can be used by sample handling robots to provide special handling to difficult shaped tubes. For example, a rounded-bottom tube can be inserted into a slot with a slight lean as long as the slot has a chamfer. The chamfer will convert the downward force into a lateral correcting force due to the rounded shape. With flat-bottom tubes, the correcting effect of a chamfer will not be realized. Therefore, flat bottom tubes may require additional placement efforts before declaring seating properly to avoid a fatal processing error. The shape of the bottom can also be used to determine fluid volume when the size of the tube and fluid level are determined.

In some embodiments, imaging devices in a characterization station can visually confirm that a sample vessel has been fully seated on the bottom of a carrier. This may be important if tubes can be manually placed onto carriers by operators, because this greatly increases the chance that a tube will not be properly seated. Improperly seated tubes can experience unsafe forces moving around an automation system and may lean, fall over, or be ejected. A leaning tube may cause a pipette or robotic arm to jam. An improperly seated tube could also cause errors in tube height measurement or sample volume determination.

In some embodiments, IR sensitive optics can be used to detect the temperature of a sample vessel and/or the fluid within the vessel. This information can be used by analyzers to adjust calibration curves to account for shift in temperature from nominal temperature. This may be useful because chemical reactions may occur at different speeds at different temperatures. By identifying the temperature of the sample vessel at a characterization station, lower cost sensors in analyzers may be used, because the analyzer may not need to perform the temperature measurement for each reaction.

In some embodiments, multiple types of carriers can be used within the automation system. For example, some carriers may include a single slot for a sample, some may include multiple slots, some may carry reagent packs, or some may be configured to perform maintenance tasks. In some embodiments, the characterization station may visually inspect each carrier to determine salient features that can allow a processor to recognize the type of carrier being characterized.

In some embodiments, the characterization station can determine properties or errors in blood samples. For example, images can be processed to determine the presence of gel barriers between serum and the rest of the blood in centrifuged samples. Serum is often extracted from whole blood through centrifugation. Tubes that need to be centrifuged often contain a gel at the bottom which has a lower density than red blood cells and a higher density than serum. The forces experienced inside of a centrifuge cause the gel to reflow above the red blood cells and below the serum, forming a barrier that keeps the serum and red bloods cells separated for a period of time long enough to perform testing. It is desirable that pipette not puncture the gel barrier because it could cause red blood cells to pour back into the serum, polluting the sample and generating an invalid test result. This can also clog up the pipette. In some embodiments, the characterization station can help prevent this error from occurring by detecting the level of the gel barrier inside of the tube and reporting it to the analyzer stations.

In some embodiments, the characterization station can be used to optically detect errors in blood samples. For example, blood clots in a sample vessel may be optically detected. In the prior art, blood clots are detected by an analyzer when it attempts to aspirate a patient sample for a test and the pipette becomes obstructed. This can clog up the pipette causing the analyzer to go offline and require cleaning or maintenance. This can cause delays, because the lab may need to manually filter the sample or get a new vial of a patient's bodily fluid. This early notification could make a critical difference in patient care and may make it easier for the lab or hospital to manage errors.

In some embodiments, the characterization station can be used to optically detect hemolysis, icterus, and lipemia (HIL) in a sample vessel. In the prior art, HIL are detected by an analyzer when it attempts to aspirate a patient sample for a test. A sample with HIL cannot be processed, causing a delay in test results for that sample, because the lab needs to get a new vial of a patient's bodily fluid. This early notification can make a critical difference in patient care and certainly makes it easier for the lab/hospital to manage errors. Clots and HIL may be detected optically by observing anomalies in images of blood samples, such as discoloration, milky qualities, or heterogeneous densities.

Figure 8:
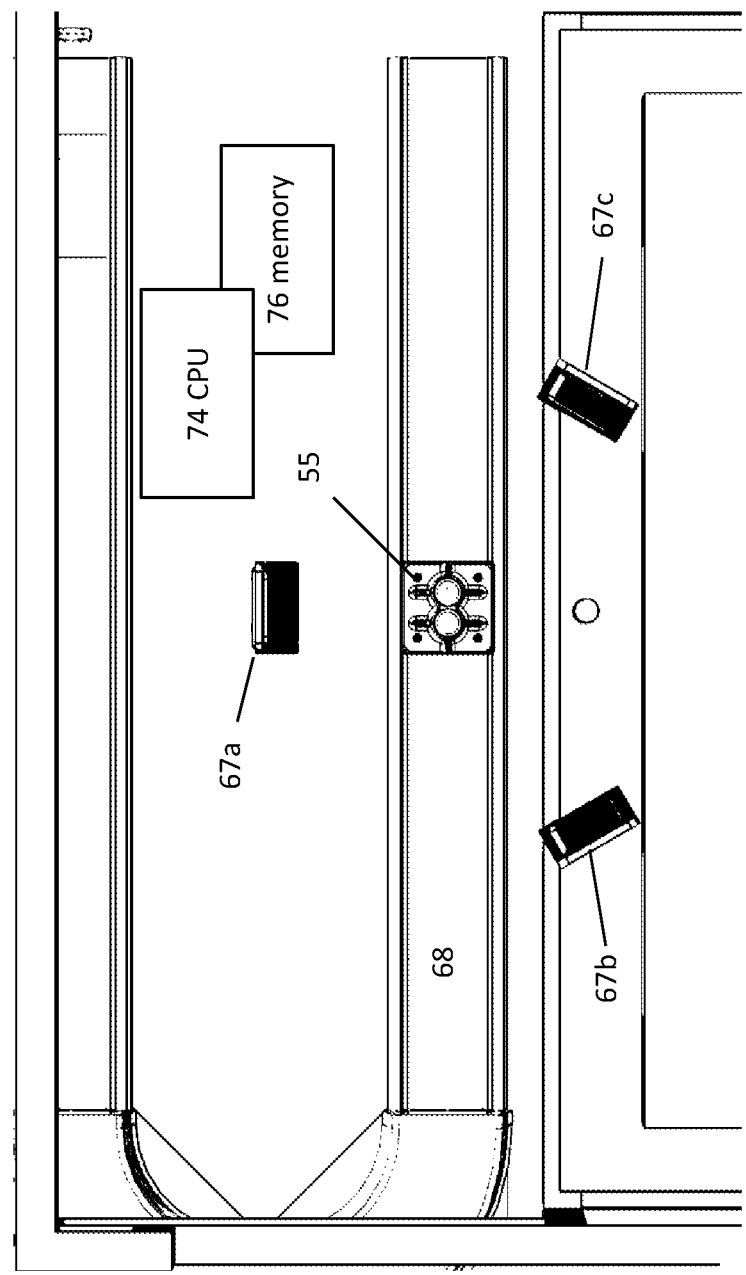
FIG. 8 is a top view and system diagram of an exemplary characterization station for use with some embodiments.

FIG. 8 shows an exemplary overhead view of a characterization station for use with some embodiments. A plurality of imaging devices, in this example, cameras 67A, 67B, and 67C, are positioned to provide various perspectives of a carrier 55 on an automation track 68. In this example, camera 67A provides a lateral view of a carrier 55 while cameras 67B and 67C provide oblique views of the fore and aft portions of carrier 55. Carrier 55 may move along automation track 68 to the position shown in FIG. 8. Cameras 67A-67C will capture images of the carrier. These images may be transmitted to CPU 74 and memory 76. CPU 74 may act as an image processor to analyze the images captured by the imaging devices to identify salient features, such as structural elements of the carrier and a sample vessel. Salient features may include sidewalls of a sample vessel, tines of a carrier that hold the sample vessel, the top edge of the sample vessel, a cap placed on the sample vessel, a tube-top cup based in the sample vessel, a barcode placed on the side of a carrier or sample vessel, a meniscus in a sample vessel indicating the top of a sample, etc. CPU 74 may determine the physical attributes of carrier 55 and any sample vessels carried thereon and the identity of the sample vessel or carrier. The identity of the sample vessel or carrier can be associated with the physical attributes that are determined from the image. This association can be stored in memory 76 for access by other portions of the automation system. For example, a sample's barcode identity may be associated with the height and width of the sample vessel, as well as the state of the sample, including whether it has a cap or tube-top cup, the height of any fluid sample contained, the longitudinal or lateral offset of the sample vessel relative to structures in the carrier, etc. This information may be used for precisely positioning a carrier when interacting with each sample vessel at subsequent processing stations within the automation system.

The association of physical attributes with the sample vessel may also be useful in routing the sample vessel within the automation system. For example, reading a barcode placed on a sample vessel can create an association between each carrier and that sample vessel, allowing the carrier to be directed to destinations intended for the sample vessel. Similarly, where a sample has yet to be de-capped, the association of the sample with a sample vessel having a cap can cause the automation system to update the destination of the sample to a de-capper before sending the sample to other locations, such as testing stations.

By associating attributes determined from images with each sample vessel or carrier in memory 76, a single characterization station can be used for the entire automation system. This can allow a central location for characterizing all important attributes of a sample vessel. This may allow significant cost savings and performance advantages over some prior art approaches. For example, whereas typical prior art automation systems require barcode readers throughout the automation system as well as mechanical mechanisms to rotate each sample tube to orient the barcode for the reader, a single characterization station can read barcodes on sample tubes without rotating these tubes due to the multi-angular perspective in the images. By associating the identity of each sample with a carrier, each carrier can convey its identity using any suitable means including RFID or optically, via fixed orientation planar surfaces. Furthermore, whereas typical automation systems may utilize mechanical means for determining tube diameters, a characterization station that optically determines diameters of sample vessels can provide a greater range of available tube diameters, without limiting diameters based on physical limitations. Optical devices, such as cameras, may be faster than mechanical sensors. By utilizing a plurality of optical devices in a single characterization station, more expensive optics may be available in a design budget, because sensors do not need to be replicated outside of the characterization station.

New workflows can also be utilized in some embodiments, whereby tube-top cups may be used in the automation system by allowing the system to automatically detect the presence of these tube-top cups and determine a precise location of the tube-top cup relative to features of the carrier. In addition, an operator may not be required to remove all caps from tubes. While an uncapped tube may successfully traverse a traditional automation system, a capped tube may cause mechanical malfunctions if it enters a station with its cap on when the station expects an uncapped sample. In some embodiments, a characterization station may prevent mechanical failures caused by capped tubes by identifying the issue and resolving it by sending the capped tube automatically to a de-capper. In some embodiments, liquid levels may be determined optically, allowing a low-level sample to be identified before it is processed further. For example, a sample identified as having insufficient fluid levels may be flagged and sent to an operator or an automation station for placing the remaining sample fluid into a tube-top cup to be further processed by the automation system.

FIG. 9B shows an alternative embodiment for optical devices that may be used in a characterization station. In this embodiment, a plurality of mirrors or a single complex mirror 80 can be provided to allow one or more cameras coaxially aligned with camera 67A to capture information in images of both sides of sample vessels on the automation track. In this example, the front side (top of the page) of a sample tube is visible in part of the image plane while the back and sides (bottom of the page) of the sample tube is visible in the image plane due to the reflections of mirrors 80. It should be appreciated that a narrow depth of field for a single camera may be insufficient to allow a single captured image to include information about the front and back side of each sample vessel. Adjustable optics for camera 67A may allow successive images to be taken to reveal both the front and back side details of the sample vessel. Furthermore, two cameras placed at the location of camera 67 may allow multiple depths of field to be used. Similarly, a single camera may be used provided it has sufficient depth of field to capture both the front side and back side image information in a single image. These images can then be processed via an image processor that has knowledge of the geometry of the optics in FIG. 9B.

The sample embodiments shown in FIGS. 9A and 9B provide multi-angular views of each sample vessel. This can allow multidimensional orientation information about each sample vessel to be determined. For example, both X and Y positioning and tilt can be determined from the plurality of perspectives. Furthermore, a barcode that exists only on a part of each sample vessel may be viewable by at least one optical device.

Figure 10:
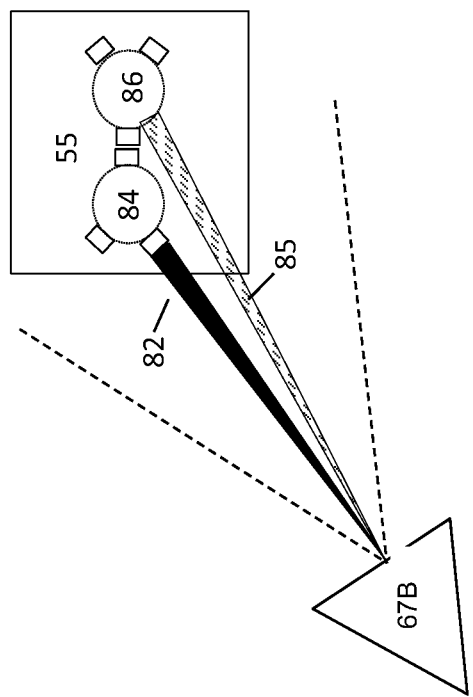
FIG. 10 is a diagrammatic top view of an exemplary characterization station for use with some embodiments.

FIG. 10 illustrates the effect placement within a carrier can have on the visibility of features of sample vessels in some embodiments. In this example, camera 67B views carrier 55. A portion 82 (e.g., a blind spot) of the view of sample slot 84 may be obscured by a tine that holds the sample vessel in a slot 84. In some embodiments, the tines that hold sample vessels in carrier 55 may extend substantially up the sides of each sample vessel. This can allow the tines to more securely hold the sample vessel within the carrier. However, typical barcodes are placed in the form of stickers manually affixed to the walls of sample vessels.

While these barcodes may extend around a substantial portion of the circumference of each sample vessel, a tine may obscure a substantial portion of that barcode. In this example, blind spot 82 may be eliminated if the sample is moved to sample slot 86. Corresponding image portion 85 allows a clear, visible line of sight between camera 67B and a sample in slot 86, without adjusting the angular orientation of the sample vessel. Accordingly, when a sample is placed in the carrier 55, a sample handling robot arm may view and consider the position of the barcode on a sample vessel and automatically choose a position within a multislot carrier, where the configuration of the slot and the orientation of the barcode provides an unobscured line of sight to cameras within the characterization station. This may allow the sample vessel to be placed into a carrier at load time in a manner that facilitates later characterization. In some embodiments, a robot arm may also be available to the characterization station to move a sample vessel from slot 84 to slot 86 if a portion of the barcode is obscured by blind spot 82. In some embodiments, an operator may be instructed to choose an orientation when manually placing a sample vessel into a sample carrier so as to avoid obscuring a label. In some embodiments, a sample handling station that places samples in each slot of the carrier may be configured to orient the sample vessel to provide clear line of sight.

Figure 11:
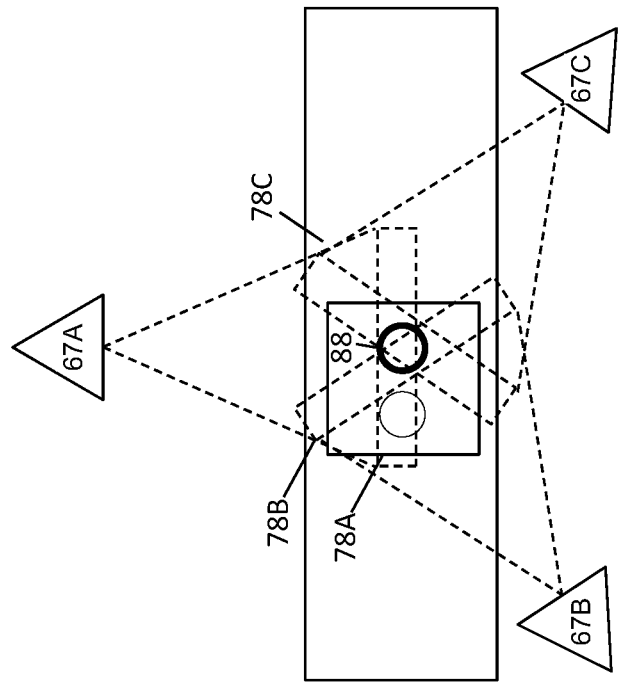
FIG. 11 is a diagrammatic top view of an exemplary characterization station for use with some embodiments.

FIG. 11 shows another exemplary configuration of a characterization station. In this embodiment, cameras 67A, 67B, and 67C include depths of field 78A, 78B, and 78C respectively which are substantially coextensive. That is, when a sample vessel 88 is placed at the intersection of the fields of view, each imaging device can capture a clear image of some or all of the salient features of sample vessel 88. When a sample is placed in another slot, the carrier can be adjusted to place a sample vessel at the location of sample vessel 88 to provide meaningful image information. In some embodiments, a processor coupled to cameras 67A through 67C can notice that a sample vessel is not at the location of sample vessel 88 and request the carrier to move that sample within the depths of field of the cameras.

Exemplary Automation System

Some embodiments may use systems and methods that provide a more efficient lab automation system to allow samples to be shuttled between and amongst various analyzer testing stations with less latency and more individual control. Exemplary systems can reduce or eliminate queues experienced by samples traversing the automation system. Samples may undergo many different types of testing in an analyzer, which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

Figure 12:
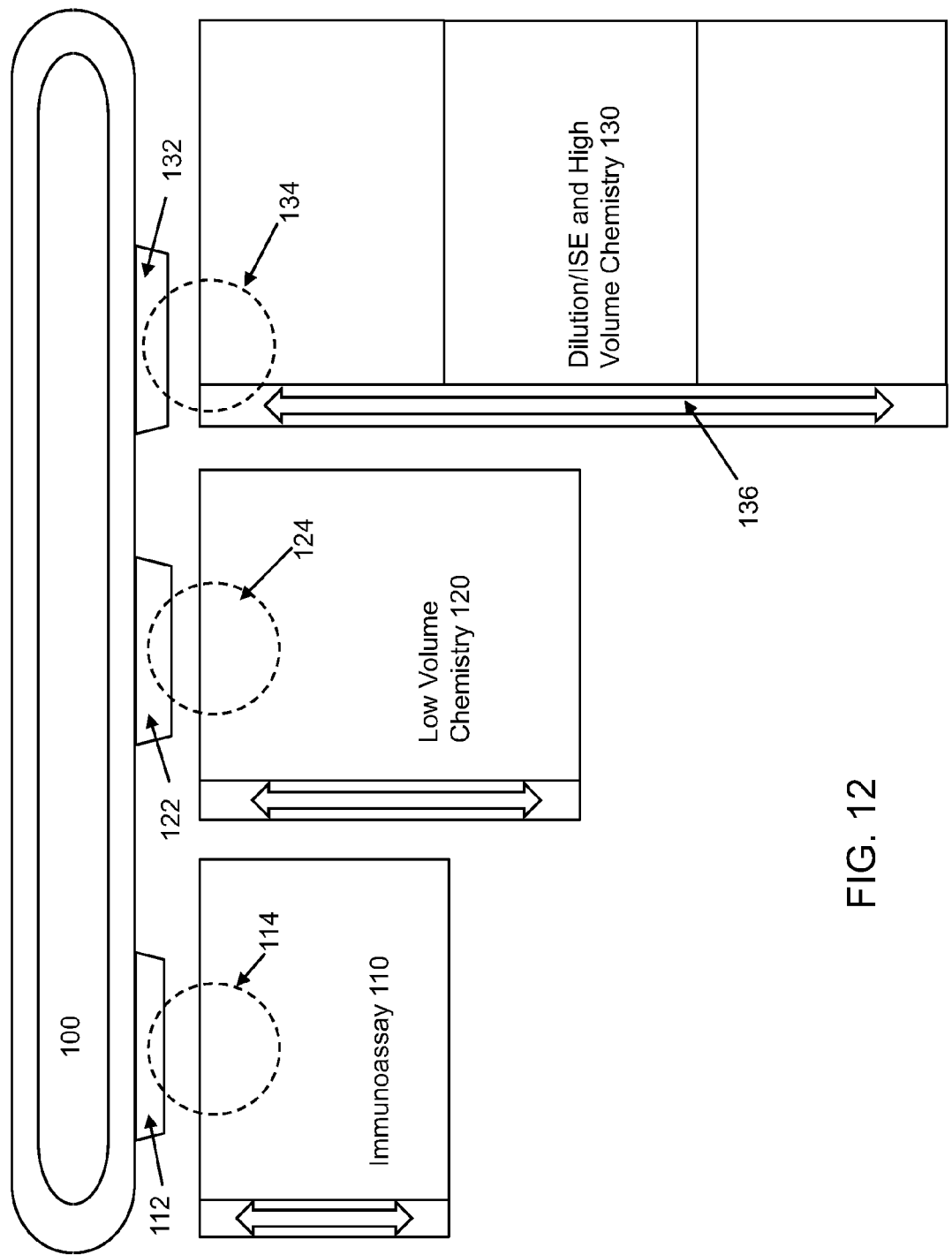
FIG. 12 is a top view of an exemplary clinical chemical analyzer geometry that can be improved by use of the automation system embodiments disclosed herein.

An exemplary track geometry, for use in transporting samples within an analyzer typical in prior art configurations, is shown in FIG. 12. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some systems, each sidecar can be serviced by a handling mechanism such as sample probe arms 114, 124, and 134. These robotic handling arms can aspirate sample material from samples in sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system may be that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm. In some embodiments, each automation track can include one or more characterization stations to provide characterization of the location and placement of each sample tube within each carrier, as the placement may change if the carrier is moved between automation tracks. In embodiments where a single track having different contiguous track sections is used, a single characterization may be sufficient. In some embodiments, multiple characterization stations are used to provide additional precision by increasing the number of measurements.

Some automation systems for analyzers can treat individual analyzer/testing stations as generic destinations for a sample on the track. In some embodiments, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 13A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload with the IVD environment, such as fluid samples, reagents, or waste. Fluids, such as patient samples can be placed in a container or vessel, such as a test tube, vial, cuvette, etc. that can be transported by a carrier. Carrier, as used herein, is a general term for pucks, trays, or the like for handling material in accordance with the disclosed embodiments. Carriers, and by extension payloads, such as sample vessels, can move on the main track 150 or be diverted via decision points such as 164 or 166. These decision points can be mechanical gates or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 13B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off the main path to a side path such as path 180. At decision point 186, a sample on the main track section 172 can be made to continue on the main track or be diverted onto path 180. Once an analyzer station along handling path 180 is done processing the sample, the sample proceeds to decision point 184 where it may be placed back onto the main path 170.

Figure 14:
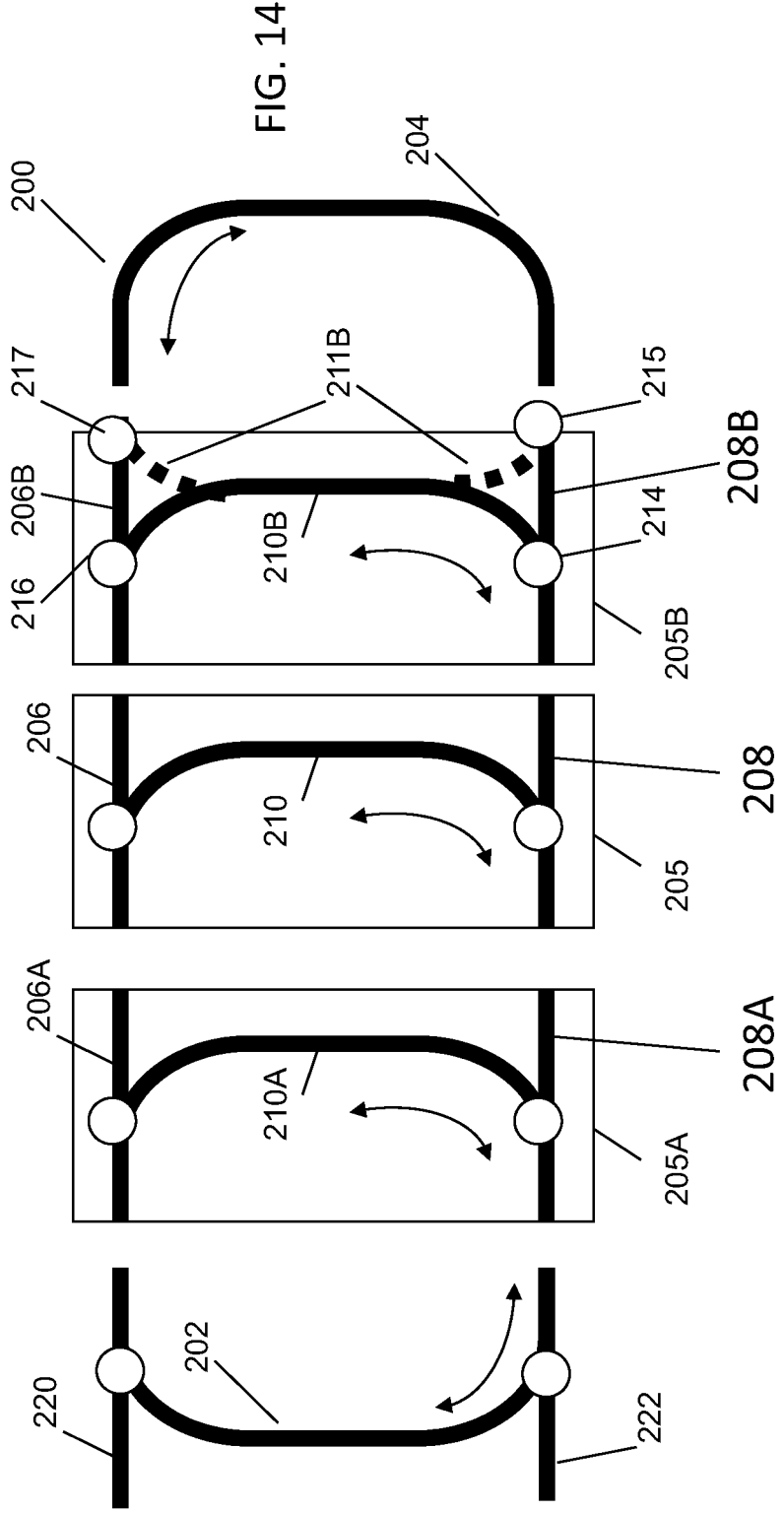
FIG. 14 is a diagrammatic view of an exemplary modular track configuration that can be used with the embodiments disclosed herein.

FIG. 14 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems. Using characterization stations and applying an offset to carriers when positioning at various stations can provide the accuracy and repeatability that may be useful for using an automation track as the primary means for positioning sample vessels within an analyzer module.

With respect to FIG. 14, the track 200 can be broken into modular components that are integrated into analyzer modules. In this exemplary track, modules 205, 205A, and 205B can be combined with one another and optionally other modular track components 202 and 204 to form a track similar to that shown in FIG. 13B. For instance, 205A can be a module that performs the same function as immunoassay 110 (FIG. 12), 205 can be a module that performs the same function as low-volume chemistry module 120 (FIG. 12), and 205B can be a module that performs ISE electrolyte testing, like module 130 (FIG. 12). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, may be that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle time or demand varies between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical random access queue found in analyzer modules. By aliquoting a portion of a sample into one or more vessels in a carousel ring, an analyzer module can select any of a number of samples to process at any time within the analyzer. However, carousels may have drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other physical RA queues can be eliminated from the modules and the sub-paths (e.g., 210) from the automation system can be used as part of an RA or FIFO queue. That is, if the travel time for a sample between any two points can be bound to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample-under-test. Once that sample-under-test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample-under-test is required to be at a module for longer than an operation cycle, or if multiple samples will be processed by the module during an operation cycle, the sub-path 210 can act as a queue for the module.

In some embodiments, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving modules knowledge of the arrival time of a sample, each module can prepare resources and interleave tests or portions of tests to more efficiently allot internal resources. In this manner, modules can operate on samples in a just-in-time manner, rather than using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points, such as decision points 214 and 216, can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing "just-in-time" access to a STAT sample without otherwise disrupting the operation of each analyzer module.

Modular design can also allow certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 14 and FIG. 13A and FIG. 13B can be operated independently from one another, or can be passive. Independent carrier movement can provide advantages over friction-based track systems (such as non-localized conveyor belts where the entire friction track must be moved to effect movement of a sample carrier). This means that other samples also on that track must move at the same rate. This also means that if certain sections operate at different speeds, collisions between passive carriers carrying samples can occur.

Figure 15A:
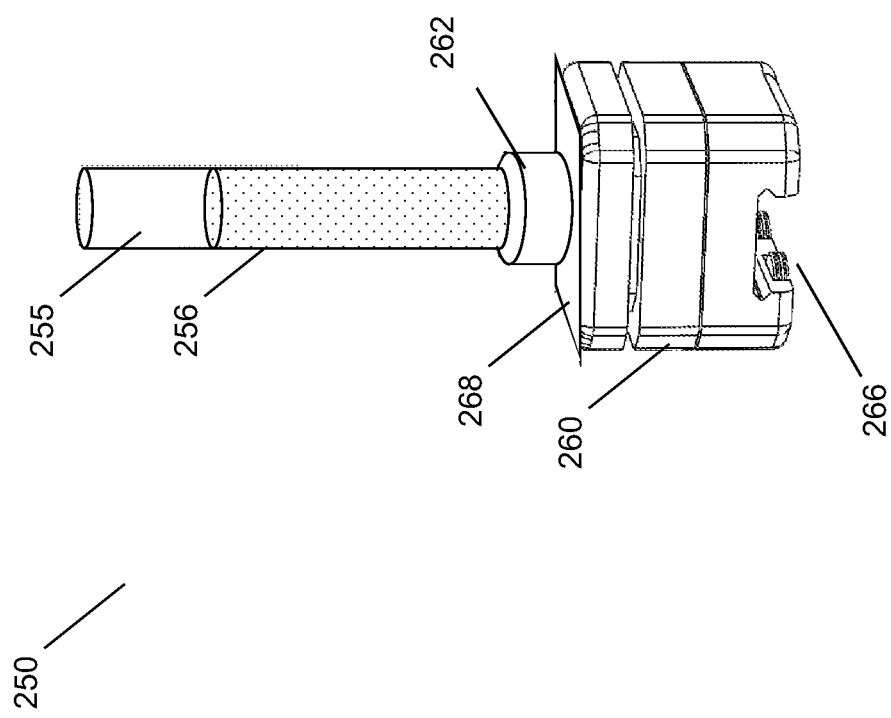
FIG. 15A is a perspective view of an exemplary carrier that can be used with the embodiments disclosed herein.

FIG. 15A depicts an exemplary carrier 250 for use with some embodiments of the present invention. Carrier 250 can hold different payloads in different embodiments. One payload can be a sample tube/fluid container 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 is supported by guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display 268 on the top of the carrier 250, the status information can be viewed at a glance by an operator. This can allow an operator to quickly determine which sample he/she is looking for when there are multiple carriers 250 in a group. By placing the rewritable display 268 on top of the carrier 250, an operator can determine status information even when multiple carriers 250 are in a drawer or rack.

Figure 15B:
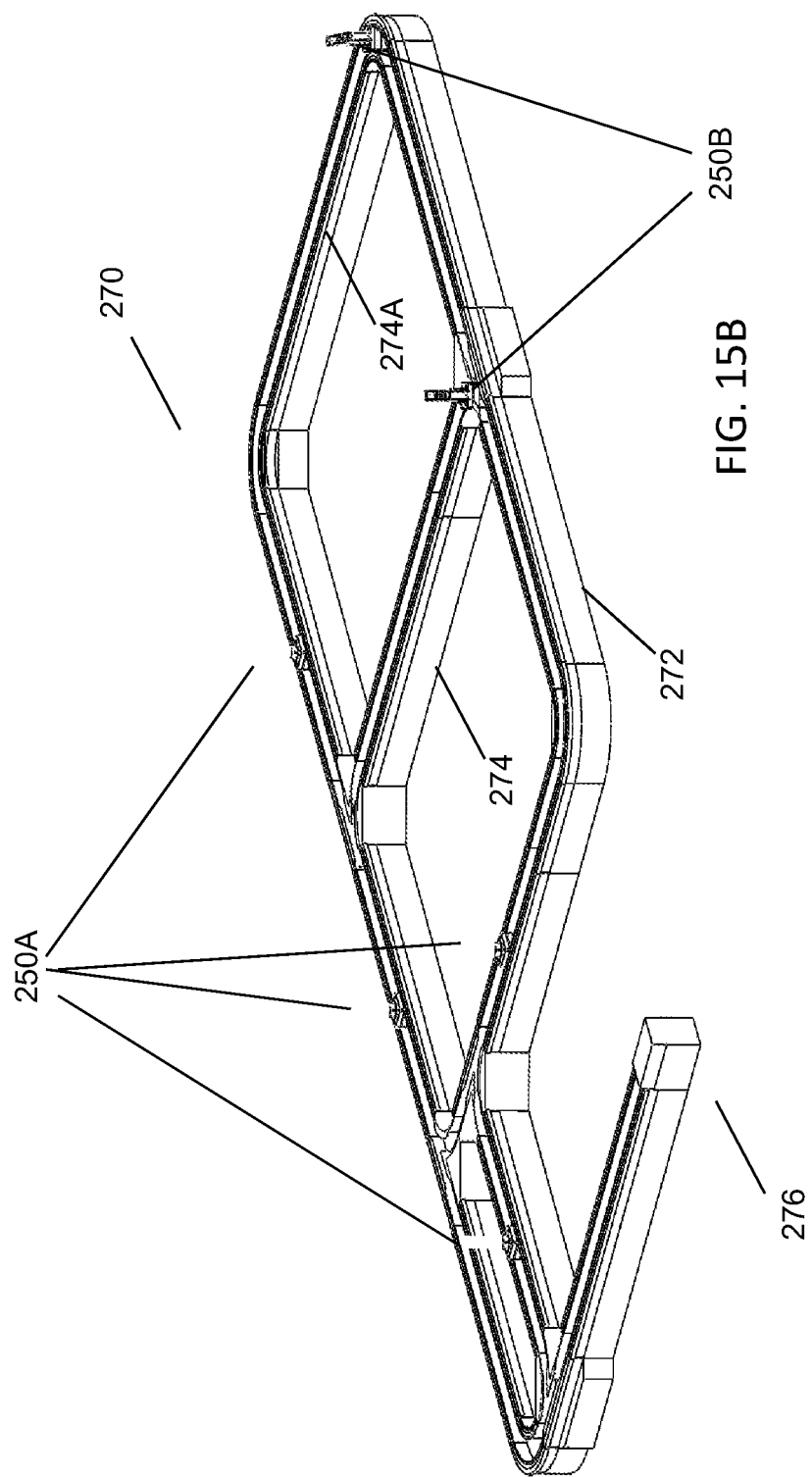
FIG. 15B is a perspective view of an exemplary track configuration that can be used with the embodiments disclosed herein.

FIG. 15B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 15C:
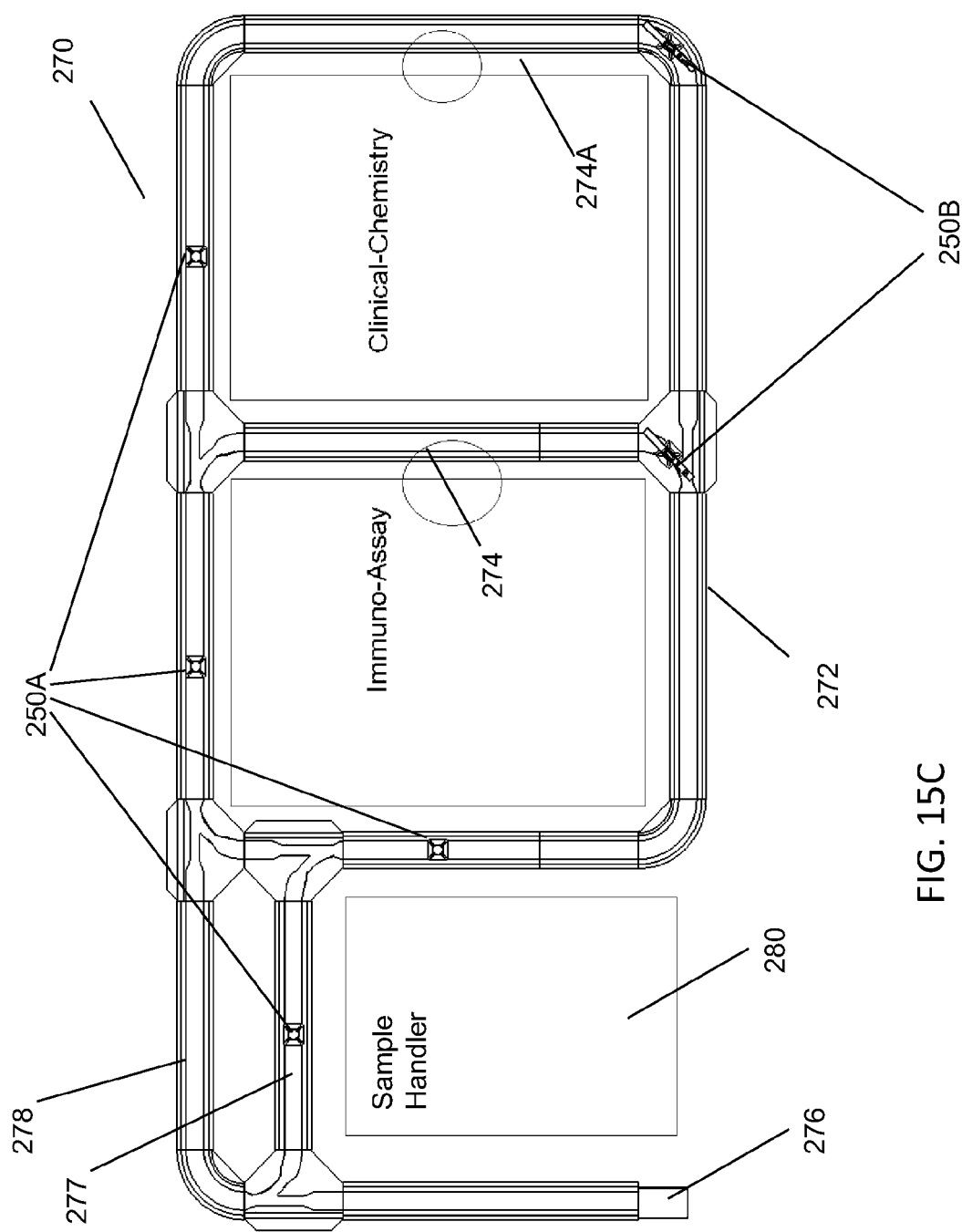
FIG. 15C is a top view of an exemplary automation system that can be used with the embodiments disclosed herein.

FIG. 15C shows an additional view of an exemplary track configuration 270. In this example, sub-path 274 serves an immunoassay station, while sub-path 274A serves a clinical chemistry station. Input/output lane 276 can be served by a sample handler station 280 that uses sub paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

In some embodiments, intelligent carriers can enable certain improvements over passive pucks on the friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a processor coupled to a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

In some embodiments, by moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

In some embodiments, by allowing carriers to move independently, carriers can move around the track faster. One limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For friction-based track systems, the velocity of the track should be limited to prevent acceleration and jerk experienced by pucks from exceeding threshold amounts because the entire track moves. However, by using a track system with independently operating sections that can respond to individual carriers, or individual carriers that have autonomous motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, in some embodiments, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

In some embodiments, an autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and know its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

In some embodiments, once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Each carrier operates independently from one another, a carrier can do this quite quickly without necessarily stopping at each decision point and without waiting for other carriers in a queue. Because these carriers can move quickly, there may be less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in U.S. Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier. In some embodiments, tracks move with more precision near instruments.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 16:
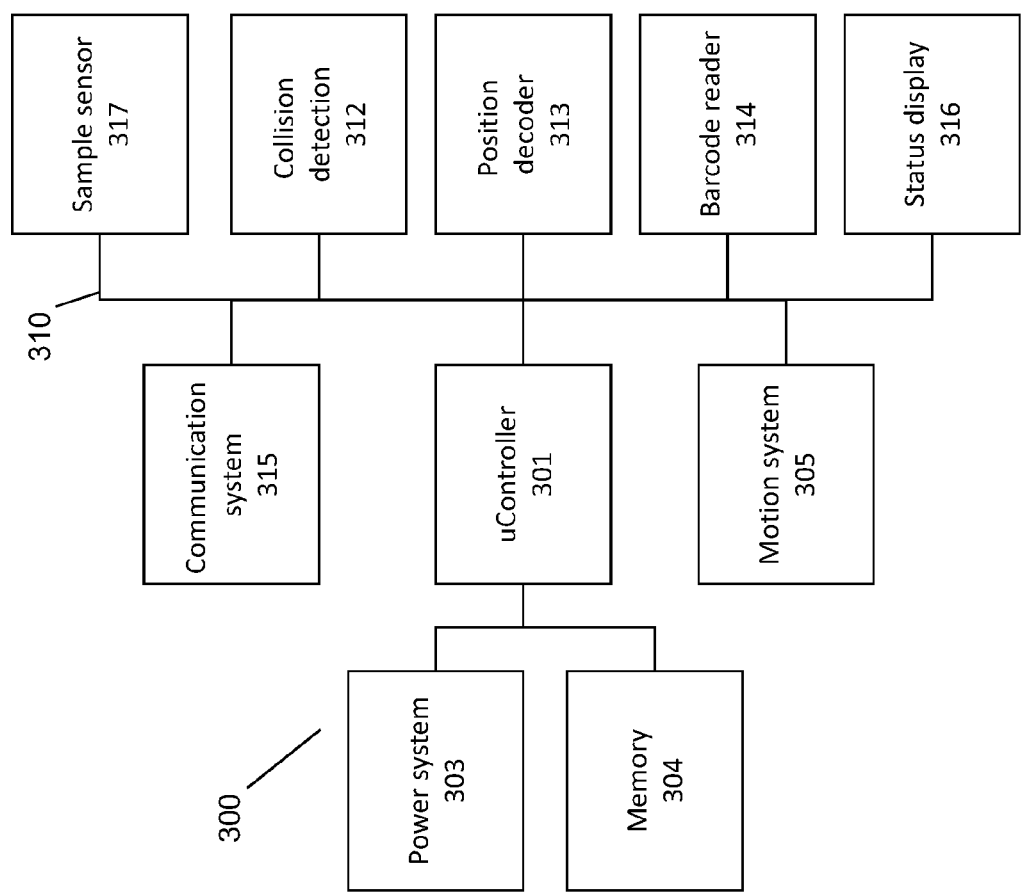
FIG. 16 is a system block diagram of the control systems including onboard active carriers that can be used with certain embodiments disclosed herein.

FIG. 16 shows a top level system diagram of the control systems and sensors for an intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication, or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket. In some embodiments, this is a momentary mechanical switch that is depressed by the presence of a tube and not depressed when a tube is absent. This information can be used to determine the status of a tube, which can assist in the display of status information by status display module 316.

Routing

In some embodiments, substantially instantaneous trajectory observation and control is conducted on-board each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 17:
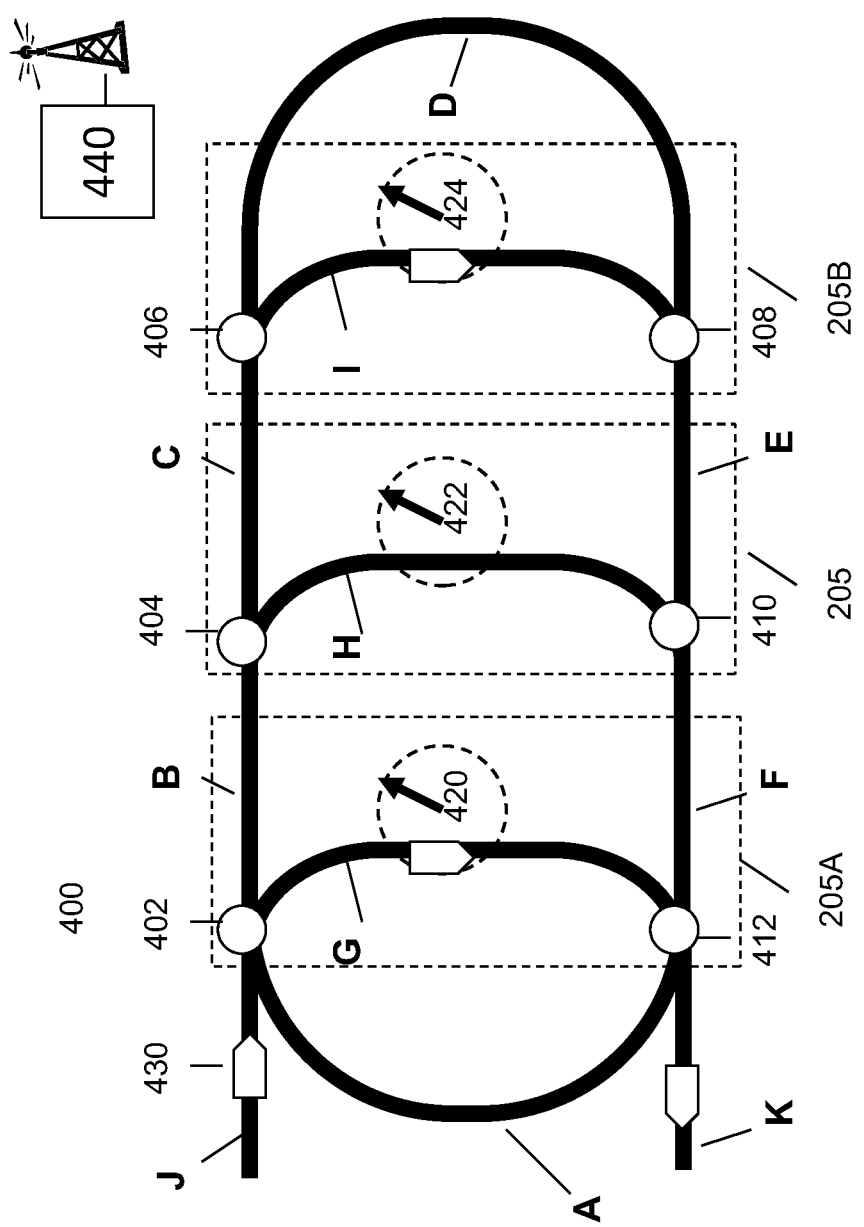
FIG. 17 is a diagrammatic view of exemplary routes in an exemplary track configuration that can be used for navigation of sample carriers in certain embodiments.

FIG. 17 shows an exemplary routing scenario in automation system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track 400 shown in FIG. 17 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 12. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

Central management processor 440 can instruct carriers to stop at positions to interact with pipette 420, 422, or 424. By utilizing a characterization station to characterize offsets between the position of sample tubes carried by a carrier and some known position on the carrier, such as the location on a carrier that would ordinarily come to rest at a fixed stopping position to interact with each of these pipettes, central management processor 440 can instruct carriers or local track resources interacting with the carriers to stop the carrier at a position that compensates for any measured offset. This can allow pipettes 420, 422, or 424 to repeatably interact with sample tubes at fixed locations on the respective track sections, even though carriers transporting the sample tubes may come to rest at locations that vary from carrier to carrier.

In some embodiments, carriers can utilize local track encoding around the pipettes to assist in accurately placing the carrier at a stopping position that compensates for measured offsets. Encoding can include optical marks or the like and localized encoding may assist in positioning the carrier at a desired position that is incrementally spaced from an optical mark. In some embodiments, magnetic positioning may be used whereby Hall effect sensors can accurately measure the current location of the carrier and electromagnets can be used to maneuver carrier to a final resting position with fine precision. In some embodiments, the incremental distances that may be used to position a carrier relative to a fixed stopping point may be less than 1 mm. Suitable encoding schemes that may be used for encoding position information, as well as offsets from known positions, may include those encoding schemes described in U.S. Provisional Patent Application No. 61/651,296, filed May 24, 2012, which is incorporated herein by reference in its entirety.

In some embodiments, local track sections behave differently from main track sections, allowing finer precision when placing carriers at locations to interact with instruments. For example, main track section may be capable of positioning a carrier with large resolution, such as several inches, whereas a local track section may include finer precision components that allow a carrier to be positioned within fractions of a millimeter.

Utilizing a Characterization Station with an Automation System

Figure 18:
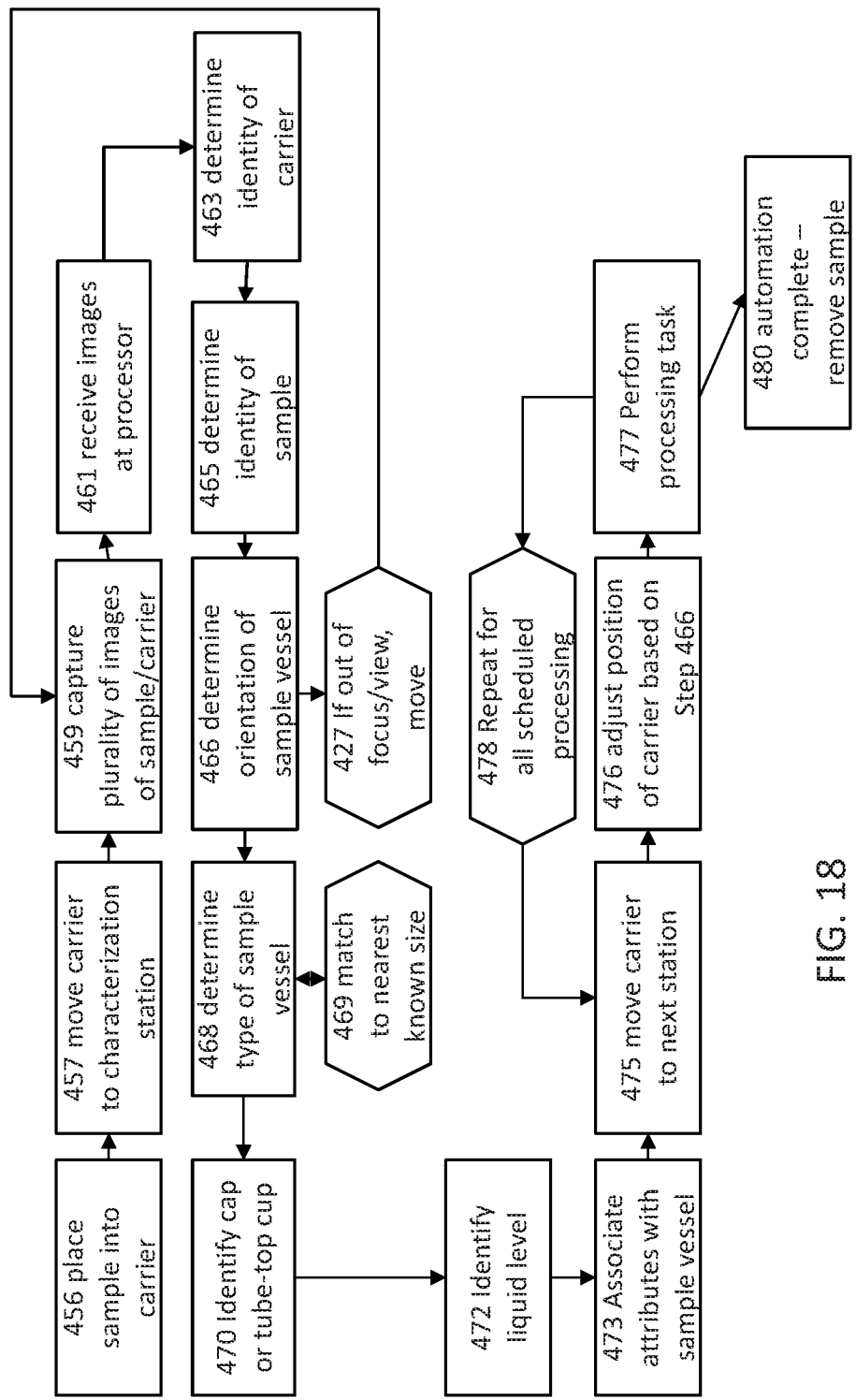
FIG. 18 is a flow chart of an exemplary characterization method for use with some embodiments.

FIG. 18 shows an exemplary method for utilizing a characterization station to determine certain characteristics of carriers or sample vessels. At step 456, an operator or sample handling unit places a sample into a carrier on an automation track. At step 457, the carrier is moved along the automation track through motive force provided by the carrier or the automation track to a characterization station. After moving, the carrier and payload may be positioned at an imaging location where one or more imaging devices in a characterization station may capture one or more images of a carrier and/or payload. In some embodiments, the carrier may be stopped at the imaging location prior to images being taken. In some embodiments, images may be taken while a carrier is moving. It should therefore be appreciated that in some embodiments, the following steps occur after the carrier has stopped at an imaging location or while the carrier is moving through the image location, depending on the embodiment.

At step 459, the characterization station captures a plurality of images using a plurality of optical devices. These images capture features of sample vessels or carriers in their field of view. At step 461, a processor receives these images. These images are received from the plurality of optical devices from the characterization station. In some embodiments, the processor is part of the characterization station, while in other embodiments, the processor may be external to the characterization station. These images can include a plurality of perspectives of each sample vessel or carrier on the automation track.

At step 463, the processor begins performing a number of automatic analysis steps. At step 463, the processor determines the identity of the carrier. At step 465, the processor determines and identity of the sample. This can occur by determining which features in the plurality of images corresponds to barcode information or other digital marks. When these marks are read, an identity of the sample vessel, such as related patient information, can be retrieved. Steps 463 and 465 can be performed alone, alternatively, or in combination. For example, a data record that associates a carrier identity to its payload can be used to identify the sample/payload once image processing reveals the identity of the carrier at step 463, or vice versa if the image reveals identity information about the identity of sample at step 465. At step 466, the processor determines the orientation of the sample vessel. This orientation can include XYZ translation or position or tilt information. At step 467, the processor determines if there is insufficient information in the images received, such as the sample vessel or carrier is out of view or out of focus, the carrier moves at step 427. If so, the processor sends a signal to one or more processors that control the carrier or automation track to move the carrier into a suitable position, allowing step 459 to repeat to capture a plurality of images of the shifted sample and carrier.

At step 468, the processor automatically determines the type of sample vessel or dimensions. By identifying salient features, such as edges, in the images, the processor may determine the size characteristics of the sample vessel. Optionally, at step 469, the processor may compare the observed dimensions of a sample vessel to a list of available tube types and their dimensions. The processor may match the dimensions observed to the most likely candidate sample tube type based on dimensions. In some embodiments, the dimensions of the sample tube type may be substituted for the observed dimensions to allow for some error in the image.

At step 470, the processor analyzes the images to determine if a cap or tube-top cup is placed on the sample vessel. If a cap is placed on the vessel, characteristics of the cap, such as the pattern or color of the cap may be used to identify certain information about the contents of the sample vessel, such as fluid type. This information can later be used to determine subsequent handling steps for the sample vessel. At step 472, the processor continues the automatic steps and identifies a liquid level in the images. This may occur by observing a meniscus edge in the image, or by observing color changes or saturation changes in various areas of the image area at step 473, the processor automatically associates the characteristics determined in steps 463 through 472 with the sample vessel or carrier. This association may be made in a database that is accessible to other processors within the automation system. For example, a database may be shared amongst various stations in an automation system, allowing an identification of the carrier at each station to be used to identify the various characteristics of the carrier and sample vessel that were determined by the characterization station. This information may be useful, for example, for precisely positioning the center of a sample vessel within a handling station based on orientation information determined at step 466.

At step 475, the automation system moves the carrier to the next station in the automation system. For example, the carrier may be moved to a de-capper station if a cap is observed in step 470. Similarly, if no cap is observed in step 470, the sample may be moved to a testing station based on the identity of the sample determined at step 465.

In some embodiments, a station within the automation system may require accurate placement of a sample vessel. At step 476, an offset can be applied to the positioning of a carrier based on the orientation information determined at step 466. This may allow, for example, a pipette to have a line of action substantially near the center of a sample tube based on the characterization by the characterization station.

At step 477, the processing task by each station is performed on the carrier and or sample vessel. Steps 475 through 477 are repeated, at step 478 for all scheduled processing. This can include moving a sample to each station within an analyzer to perform an entire test panel, as defined by information in a laboratory information system database that is associated with the identity of the sample determined at step 465. At step 480, automation is complete, and the sample is moved to a sample handler station to be removed from the automation system and placed into storage.

Figure 19:
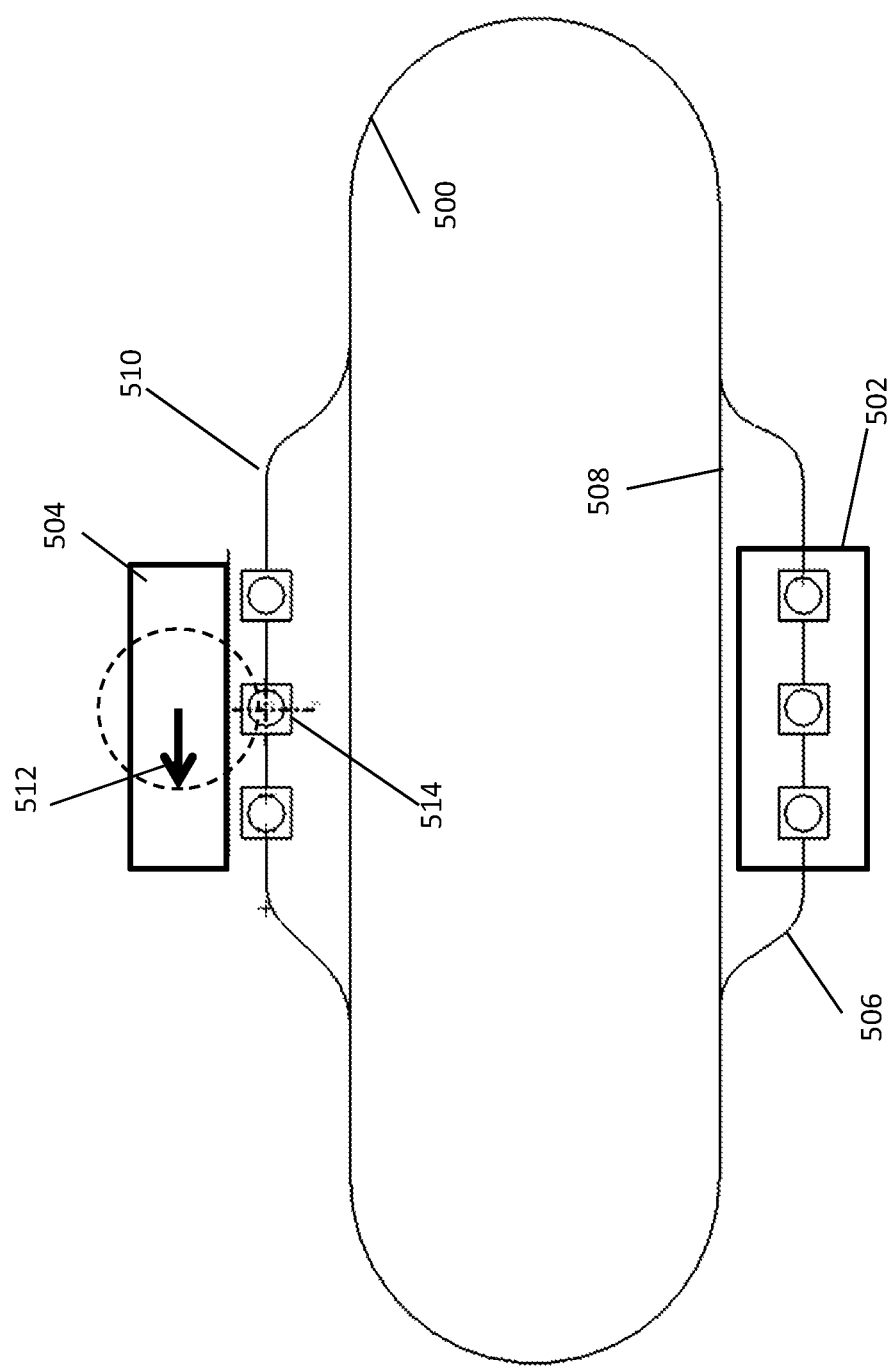
FIG. 19 is a top view of an exemplary automation track for use with some embodiments.

FIG. 19 shows an exemplary illustrative track 500 that includes a characterization station 502 and a sample processing station 504. It should be appreciated, that in most embodiments, a plurality of sample processing stations may be used, allowing samples to interact with multiple stations to perform various tests. In this illustrative embodiment, characterization station 502 is served by sidecar 506, which allows samples to enter the characterization station from the main track, rather than proceeding on track 508. Processing station 504 is serviced by sidecar 510. Characterization station 502 can characterize the geometry of each carrier and or the geometry of samples relative to positions in the carrier. Once a carrier is characterized, the carrier can proceed to processing station 504 where pipette 512 can access a sample transported by carrier. For example, carrier 514 may be characterized by characterization station 502 to determine an offset in the normal stopping position for the carrier when the carrier 514 visits processing station 504. Once an offset is determined, carrier 514 can stop a predetermined distance from a stopping position, such as an optical mark, Hall effect sensor, or magnet, which will allow the center of a sample tube transported by carrier 514 to come to rest at a nominal stopping position for interaction with pipette 512.

Figure 20:
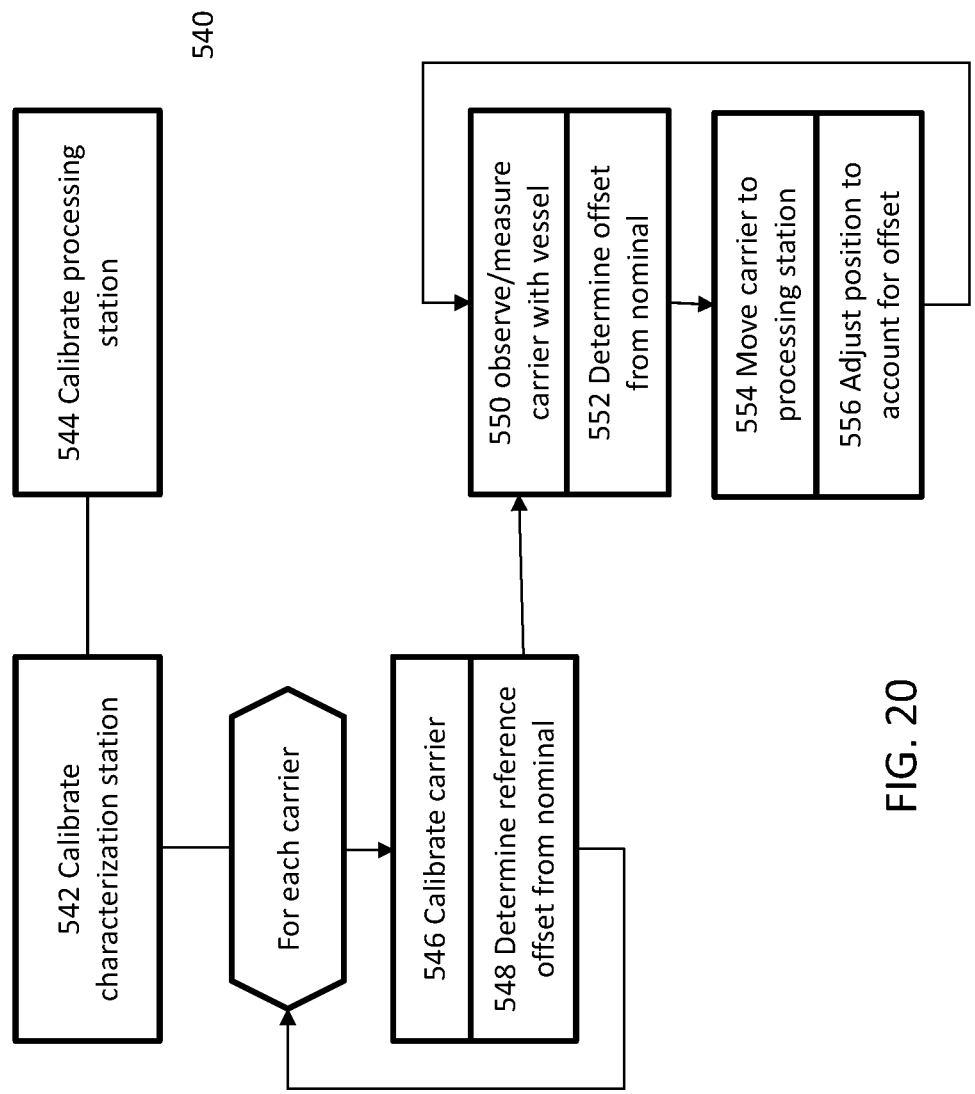
FIG. 20 is a flow chart of an exemplary characterization and positioning method for use with some embodiments.

FIG. 20 shows the exemplary process flow 540 for use with some embodiments. In some embodiments, the stations that interact with samples can be calibrated during a preliminary step. This can include using a maintenance carrier or reference device to determine if the alignments between the track and components of an instrument are at nominal positions or if an offset should be considered when interacting with these instruments. For example, a pipette in a sample processing station may be ideally aligned with position "0" on the local track section, but due to manufacturing tolerances, installation problems, wear, etc., the line of action for the pipette tip may be at a position 2 millimeters from nominal. This information can be considered when samples are handled by the pipette. For example, a carrier with nominal positioning may apply an offset of 2 mm to align the center of a sample with the line of action of the pipette.

Similarly, the calibration station itself may need to be calibrated. This can include an optical calibration whereby cameras are aligned with reference images to ensure that the calibration of each carrier corresponds with real-world offsets that should be applied to the carriers. For example, a tightly toleranced carrier can be provided as a reference carrier that can be calibrated to include known distances between a reference sample tube and a reference position on the carrier. A characterization station may attempt to characterize the reference carrier. Any errors found in the characterization of the reference carrier can be zeroed out by adjusting the interpretation of images by the calibration station. This can ensure that subsequent carriers that may be manufactured with lesser tolerances can be properly characterized by the characterization station.

In some embodiments, the calibration steps may utilize maintenance carriers, which may be manually or automatically deployed on an automation track. Suitable maintenance carriers and deployment mechanisms may include those disclosed in U.S. Provisional Patent Application No. 61/712,664, filed Oct. 11, 2012, and U.S. Provisional Patent Application No. 61/712,694, filed Oct. 11, 2012, which are incorporated herein by reference in their entirety.

At step 542, one or more characterization stations in an automation system can be calibrated to ensure accurate characterization of samples and carriers during runtime operation of the automation system. Similarly, at step 544 processing stations may be calibrated such that the line of action of any devices interacting with the automation track can be characterized and accounted for during runtime operation. In some embodiments, multiple characterization stations may be calibrated and used during runtime operations to provide further precision in characterizing samples relative to carrier positions.

In some embodiments, multiple calibration steps may occur for other components of the system, such as the automation track and any components that provide motive forces for carriers. In some embodiments, calibration steps 542 and 544 may be repeated at regular intervals, such as daily or the beginning of each shift. In some embodiments, calibration steps are only performed during initial installation of an analyzer automation system or on-demand.

Calibration steps 546 and 548 may be performed on each carrier that will use the automation system. These steps may be performed at regular intervals or upon request. Calibration step 546 may allow each carrier to be characterized while holding a reference sample. This may allow each carrier to provide a baseline for the expected position of vessels during runtime. This calibration step can be performed by characterizing each carrier and subsequently interacting with the carrier at processing stations to verify that a line of action of an instrument, such as a pipette, coincides with the center of a reference sample vessel. At step 548, a reference offset is determined from this calibration step. The reference offset is the baseline offset that will be assumed for samples carried by the carrier at runtime. It should be appreciated, that the reference offset may refer to a single edge of a tube or the center point of a tube, which may vary depending on tube size. Accordingly, a plurality of reference offsets may be calculated for each carrier for various standard tube-sizes that can be transported.

Determination step 548 may be carried out automatically using a processor that interacts with the automation system. This processor may be used during runtime to determine offsets and to direct carriers to specific stopping locations for interaction with instruments. This processor may also receive information from calibration steps 542 and 544. In some embodiments, the processor participates in the calibration steps 542 through 546.

In some embodiments, steps 546 and 542 are optional. In some embodiments, each time a tube is placed in a carrier the tube and carrier combination is characterized. In some embodiments, this characterization may utilize the reference offset from step 548 to compare the tube placement to the nominal tube placement determined at step 548. In other embodiments, reference offsets for each carrier are not used and each carrier vessel combination is characterized without any prior knowledge of the expected location of the vessel being carried.

At step 550, after a carrier receives a vessel, such as a sample tube, the carrier and vessel combination is characterized by at least one characterization station. This characterization station may be placed in any suitable position along the automation system, such as at a sample handling station where the tube is first placed into the carrier. In some embodiments, measurement/characterization step 550 can occur multiple times at multiple calibration stations. In some embodiments, calibration stations may be provided for each module within the automation system, allowing each module to make an independent determination of the proper offset to use when handling the carrier and vessel on local automation tracks. In some embodiments, step 550 occurs immediately before the carrier is placed in position to interact with an instrument, such as a pipette. This may allow the most up-to-date offset to be used.

Measurement/characterization step 550 can include optically observing the carrier and sample vessel. Observation can include optical measurement of distances and relative locations of components of a carrier and the vessel being transported. This can include using an electro-optical device, such as a camera, a laser and photo detector, IR rangefinders, projectors, lenses, etc. In some embodiments, measurement/ characterization step 550 can include mechanical measurements, such as feelers that determine where a carrier has stopped and where a vessel being transported has stopped in a characterization station. In some embodiments, magnetic devices, such as Hall effect sensors may be used to determine a precise location of a surface of a carrier to provide a reference position when measuring the location of a sample vessel carried by the carrier.

The observation in step 550 can include determining one or more distances between points in the carrier, such as a reference point on the carrier and the leading and trailing edge of the sample vessel. This can be used to provide a reference location of the edge or center of the vessel relative to the reference point on the carrier. By subsequently positioning the carrier and the reference point, the edge or center of the vessel can also be precisely placed. In some embodiments, measurement 550 includes detected location of an edge or center of the sample vessel in an image. This location can then be compared to the expected location of the vessel.

The observations from step 552 can be communicated to a processor. This may include local signaling with a local processor or communicating across a network to a processor for calculation of an offset to account for the observed positioning of the sample vessel.

Once the carrier and vessel combination has been measured, at step 552, a processor can determine an offset from a nominal position, or any reference point in the carrier. For example, where a carrier has been calibrated at steps 546 and 548, the carrier may include a nominal position, which is the expected position of the centerline of a sample tube being carried. The measurement received from step 550 may show a difference between the detected centerline of a sample vessel and the nominal centerline of the sample vessel. This can be added to any offset determined by step 548. In some embodiments, an offset is calculated by determining the centerline of a sample tube from step 550 relative to a reference point on the carrier. The offset may be the distance between centerline of the sample tube and the reference point on the carrier. Subsequently, when the carrier is placed for interaction with a pipette, the reference point on the carrier can be placed at a distance equal to the offset from the centerline of the center of the tube, so that the center of the sample tube and the line of action of the pipette are roughly coincident. Steps 550 and 552 can occur automatically for each sample placed on an automation system.

At step 554, the carrier is moved from the characterization station to a position to interact with one or more processing stations within the automation system. For example, this can include a station that aspirates a portion of a sample contained in a sample vessel for use in any number of suitable tests. Once a carrier is moved to the processing station, the carrier can be precisely positioned such that the center of the vessel it transports is coincident with the line of action of any instrument, such as pipettes. This can be accomplished by adjusting the reference position of the carrier by the offset calculated at step 552. Step 556 may be carried out at the direction of the processor that calculates the offset at step 552 or may be carried out by another processor that operates responsive to the offset received from a processor calculating the offset at step 552. The adjustment at step 556 can also take any calibration information derived from step 544 into account. For example, the calibration of processing station may identify the nominal position for a sample when interacting with pipette. This may be considered when calculating the final position of the carrier to align the line of action of the pipette with the centerline of the vessel being carried.

Figure 21:
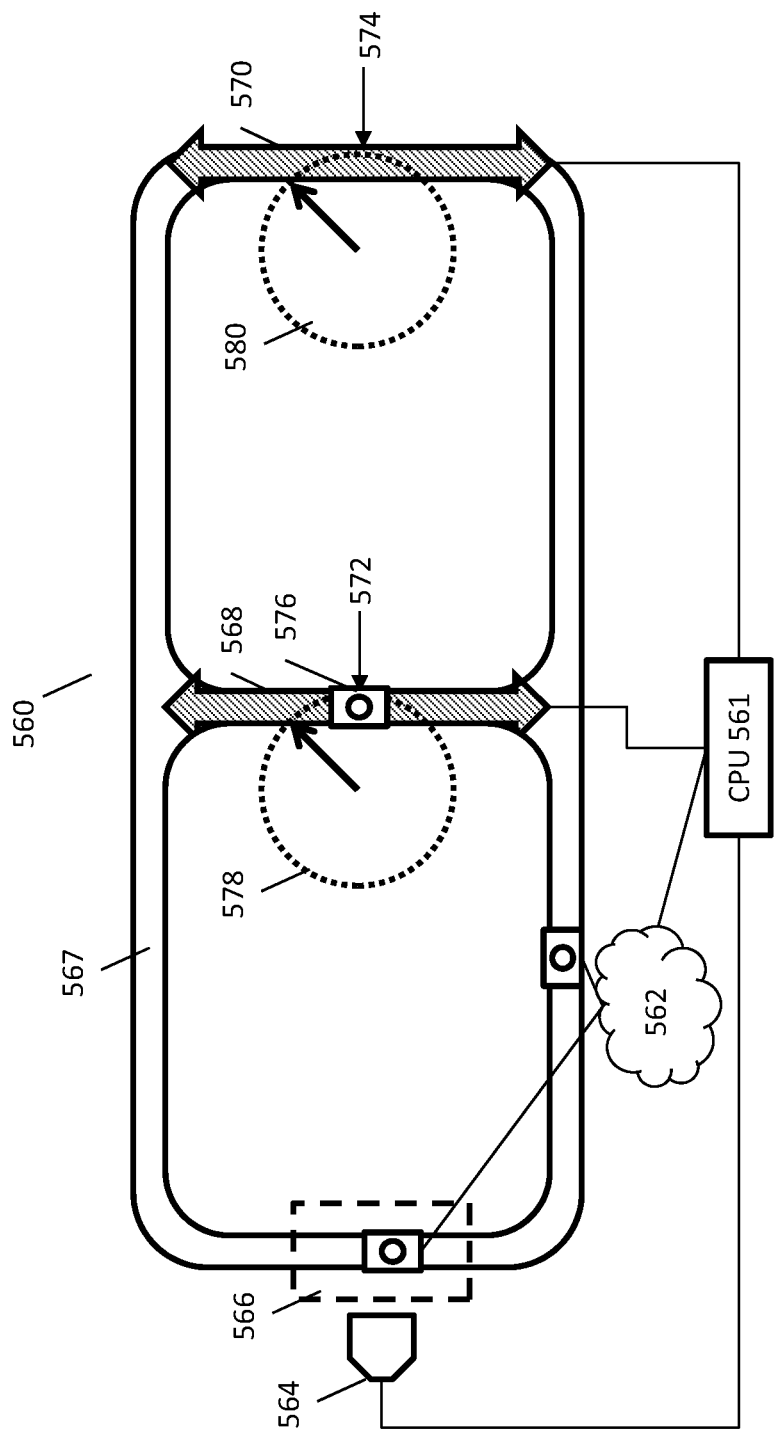
FIG. 21 is a top view of an exemplary automation system for use with some embodiments.

FIG. 21 depicts the system architecture for an exemplary system for use with some embodiments. Automation system 560 includes a processor 561 that directs the activities of the automation system. Processor 561 can interact with components of automation system 560 via network 562 or through direct connections. Network 562 can include a wireless or Ethernet-based network. Processor 561 can interact with optical devices 564, which operate as part of characterization station 566 to characterize carriers. In some embodiments, processor 561 can also communicate directly with carriers, such as carrier 576. This can allow processor 561 to issue routing instructions where carriers are configured to operate semi-autonomously and route through the automation system.

Carriers can traverse automation system 560 using track 567. Once a carrier is characterized by characterization station 566, the measurements taken by optical measuring device 564 can be communicated to processor 561. Processor 561 can then calculate an offset to apply to each carrier at each station 578 and 580 in the automation system. In some embodiments, processor 561 can also communicate with and control local track positioning devices, such as local tracks 568 and 570. These can include friction or magnetic tracks that can be operated with fine precision to precisely position carriers, such as carrier 576, at positions on the local automation track. For example, carrier 576 may be positioned at an offset from reference position 572 on track 568. Reference position 572 may be a nominal position for station 578 (or a position that should coincide with a reference position on a carrier under nominal conditions). Carrier 576 may be positioned such that a reference position within carrier 576 is placed at an offset from position 572 in accordance with the offset determined by processor 561, such that the center of a sample vessel being carried by carrier 576 aligns with the line of action of a pipette at station 578. Similarly, station 580 may have a reference position 574 which may be used for applying an offset to carriers interacting with pipettes in station 580.

In various embodiments, different characteristics of sample tubes and carriers can be detected or measured by the characterization station including, but not limited to, any number of the following characteristics, which may be physical attributes. The characteristics can generally be determined by analysis of one or more images captured by one or more cameras of the characterization station:

- determining which, if any, slots in a carrier are occupied by a sample vessel;
- an orientation of a sample vessel relative to each carrier, which may indicate that a sample tube is leaning;
- a linear offset or rotational offset relative to a nominal position of a sample vessel;
- one or more physical dimensions of at least one sample vessel carried by each carrier;
- an inner diameter or positional extents of the sample void of a sample vessel, which may be useful in determining where to locate a pipette when subsequently interacting with the sample vessel;
- an identification of a type of sample vessel carried by each carrier;
- an identification of a type of each carrier;
- an identification of the shape of the bottom of a sample vessel carried by each carrier;
- a determination of whether a sample vessel carried by each carrier is properly seated;
- a temperature of a sample vessel carried by each carrier, which may be determined via an infrared optical device (this may be useful in improving reliability of tests or handling devices);
- a fluid level or fluid volume of a fluid contained in a sample vessel carried by each carrier (which may be qualitative, such as determining if sufficient levels exist for testing, or quantitative, such as determining an actual volume or number of tests that can be performed, the resolution of which may be improved with better images or better models of sample vessels);
- a determination of the presence of at least one of the following within a blood sample carried by at least one carrier: a gel barrier, clotting, hemolysis, icterus, and lipemia (this may be determined by observing anomalies in images, such as discolorations and inconsistent contrast within a sample);
- an identification of whether a cap is placed on a sample vessel carried by each carrier;
- an identification of at least one of a color and a type of the cap;
- an identification of whether a tube-top cup is placed on a sample vessel carried by each carrier;
- an identification of a type of the tube-top cup;
- barcode information encoded on at least one of a sample vessel carried by each carrier (which may be determined via a laser barcode scanner or via optical analysis of image);
- barcode information encoded on each carrier (which may be determined via a laser barcode scanner or via optical analysis of image);
- detecting bubbles or foam on top of a sample, which may indicate sample mishandling;
- sample fluid color, which may be useful in confirming that the sample is likely what it purports to be or if the sample may be erroneous or compromised;
- detection of peeling or misapplied barcode labels, which may be observable if the barcode fails to lay flat against the sample vessel or carrier surface (this may prevent sticky labels from interfering with other components in the analyzer);
- detection of the presence of condensation on the sides of a sample vessels, which may appear as droplets or fogging on the inside of the vessel;
- detection of the type of material of the sample vessel, which may be determined to the extent that a material, such as some plastics respond differently to polarized light or fluoresce under UV light;
- detection of damage to the vessel, such as visible chips and cracks in the vessel;
- detecting wear to barcodes labels or other data marks (these may have redundant information, allowing robust reading, but optical analysis or reading of false bits can indicate that the redundancy is being compromised);
- detecting fluid spills on carrier surfaces, which may appear as shiny or discolored portions on the surface;
- detecting wear or damage to support tines or springs that hold a sample vessel in a carrier (this may be determined by observing that tines are out of expected alignment or that tubes consistently rest anomalously close to or far from a support tine, which may indicate wear to at least one spring and demonstrate that future vessels will not be centered or will be loosely held, and allow replacement before a problem occurs); and
- detecting debris in tube carrier slots when a carrier is empty (debris can be observed in images of the tube slot when a sample vessel is not present or determined by consistently finding samples are nor seated properly when images of a carrier containing a vessel are analyzed).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations that fall within the true spirit and scope of the invention.

We claim:

1. An automation system for use in an in vitro diagnostics setting comprising:
    an automation track;
    a plurality of carriers each configured to carry one or more sample vessels along the automation track;
    a characterization station placed along the automation track comprising a plurality of cameras that capture a plurality of images, each camera configured to provide one or more images of each of the plurality of carriers from one of a plurality of perspectives while each carrier is at a predetermined location on the automation track such that the perspectives capture all sides of each carrier; and
    a processor, in communication with the characterization station, configured to analyze the plurality of images to automatically characterize at least one physical attribute of each carrier, including at least an orientation between the one or more sample tubes and each carrier.

2. The automation system of claim 1, wherein the orientation comprises at least one of a linear offset or rotational offset relative to a nominal position.

3. The automation system of claim 1, wherein the at least one physical attribute comprises physical dimensions of at least one sample vessel carried by each carrier.

4. The automation system of claim 1, wherein the at least one physical attribute comprises an identification of a type of sample vessel carried by each carrier.

5. The automation system of claim 1, wherein the at least one physical attribute comprises an identification of a type of each carrier.

6. The automation system of claim 1, wherein the at least one physical attribute comprises an identification of the shape of the bottom of a sample vessel carried by each carrier.

7. The automation system of claim 1, wherein the at least one physical attribute comprises a determination of whether a sample vessel carried by each carrier is properly seated.

8. The automation system of claim 1, wherein the at least one physical attribute comprises a temperature of a sample vessel carried by each carrier.

9. The automation system of claim 1, wherein the at least one physical attribute comprises at least one of a fluid level or fluid volume of a fluid contained in a sample vessel carried by each carrier.

10. The automation system of claim 1, wherein the at least one physical attribute comprises a determination of the presence of at least one of the following within a blood sample carried by at least one carrier: a gel barrier, clotting, hemolysis, icterus, and lipemia.

11. The automation system of claim 1, wherein the at least one physical attribute comprises an identification whether a cap is placed on a sample vessel carried by each carrier.

12. The automation system of claim 11, wherein the at least one physical attribute comprises an identification of at least one of a color and a type of the cap.

13. The automation system of claim 1, wherein the at least one physical attribute comprises an identification of whether a tube-top cup is placed on a sample vessel carried by each carrier.

14. The automation system of claim 13, wherein the at least one physical attribute comprises an identification of a type of the tube-top cup.

15. The automation system of claim 1, wherein the processor is further configured to analyze images to read barcode information encoded on at least one of a sample vessel, carried by each carrier, and each carrier.

16. The automation system of claim 1, wherein the plurality of cameras of the characterization station includes a plurality of cameras placed at different positions and angles relative to an imaging location of each carrier.

17. The automation system of claim 1, wherein the plurality of cameras of the characterization station includes at least one camera and one or more mirrors placed in an image plane of the at least one camera to provide different perspectives of each carrier.

18. The automation system of claim 1, wherein each of the plurality of cameras comprises optics with depths of field substantially concurrent with an expected position of features of each carrier.

19. The automation system of claim 1, wherein the automation track comprises a linear synchronous motor and the processor is further configured to calibrate a position of each carrier within the automation track.

20. The automation system of claim 1, wherein each of the carriers comprises a plurality of slots, each configured to receive one of the plurality of sample vessels.

21. The automation system of claim 20, wherein the characterization station is configured to move each carrier so that an occupied slot of the plurality of slots is located in an image field of the plurality of cameras prior to characterization of the at least one attribute.

22. The automation system of claim 1, wherein the plurality of cameras of the characterization station include at least one camera configured to view each carrier horizontally and at least one camera configured to view each carrier from above.

23. The automation system of claim 1, wherein the processor is further configured to analyze images to detect bubbles or foam on top of a fluid sample contained in a sample vessel carried by one of the plurality of carriers.

24. The automation system of claim 1, wherein the processor is further configured to analyze images to detect a color of a fluid sample contained in a sample vessel carried by each carrier.

25. The automation system of claim 1, wherein the processor is further configured to analyze images to detect a peeling or worn label on a sample vessel carried by one of the plurality of carriers.

26. The automation system of claim 1, wherein the processor is further configured to analyze images to detect the presence of condensation in or on a sample vessel carried by one of the plurality of carriers.

27. The automation system of claim 1, wherein the processor is further configured to analyze images to detect the type of material of a sample vessel carried by one of the plurality of carriers.

28. The automation system of claim 1, wherein the processor is further configured to analyze images to detect damage to a sample vessel carried by one of the plurality of carriers.

29. The automation system of claim 1, wherein the processor is further configured to analyze images to detect at least one of fluid spills, debris, and damage to support tines or springs related to at least one of the plurality of carriers.

* * * * *